United States Patent [19]

Nukui et al.

[11] Patent Number: 5,767,235
[45] Date of Patent: Jun. 16, 1998

US005767235A

[54] ANTICOAGULANT HIRUDIN VARIANTS AND METHODS FOR THEIR PRODUCTION

[75] Inventors: Eriko Nukui; Koichi Wada; Masaharu Nakano; Tadanori Morikawa, all of Takaoka; Kyoichi Kobashi, Toyama; Ryo Muramatsu, Toda; Akiko Sukesada, Toda; Satoru Misawa, Toda, all of Japan

[73] Assignees: Nippon Mining Company Limited, Tokyo; Fuji Yakuhin Kogyo Kabushiki Kaisha, Toyama, both of Japan

[21] Appl. No.: 367,758

[22] Filed: Jan. 3, 1995

Related U.S. Application Data

[63] Continuation of Ser. No. 946,303, Nov. 5, 1992, abandoned.

[30] Foreign Application Priority Data

Mar. 5, 1991 [JP] Japan ..................................... 3-063909

[51] Int. Cl.$^6$ ..................................................... A61K 38/08
[52] U.S. Cl. ........................... 530/328; 514/15; 514/16; 530/327
[58] Field of Search ......................... 530/324–328; 514/12–16, 2

[56] References Cited

U.S. PATENT DOCUMENTS 5,192,747  3/1993  Krstenansky ........................ 514/15

FOREIGN PATENT DOCUMENTS 0276014  7/1983  European Pat. Off. .
276014  7/1988  European Pat. Off. .......... C07K 7/10
9006128  6/1990  WIPO .
WO 90/06128  6/1990  WIPO .

OTHER PUBLICATIONS

Nakano et al. Peptide Chemistry, pp. 183–186 (1987).
Kobashi et al. Journal of Protein Chemistry, vol. 6, No. 3, pp. 237–244 (1987).
Jameson et al. Biochem. J., vol. 131, pp. 107–117 (1973).
R. Lee et al. (1983) *Journal of Biological Chemistry* 258:11326–11334.
C. Niehrs et al. (1990) *The Journal of Biological Chemistry* 265:9314–9318.
W. B. Huttner (1984) *Methods in Enzymology*, Academic Press, Inc. 107:200–223.

J. Messing (1983) in *Methods in Enzymology*, Academic Press, Inc. 101:20–79.
Muttner *Meth Enz 107*, 200–223.
Lee *J Biol Chem 258*, 11326, 1983.
Krstenansky et al. Febs Letters, vol. 211, No. 1, pp. 10–16 (1987).
Krstenansky et al. J. Med. Cehm., vol. 30, pp. 1688–1691 (1987).
Owen et al. J. Med. Chem., vol. 31, pp. 1009–1011 (1988).
Mao et al. Biochemistry, vol. 27, pp. 8170–8173 (1988).
Krstenansky et al. Thrombosis and Haemostasis, vol. 63, No. 2, pp. 208–214 (1990).
Maraganore et al. The Journal of Biological Chemistry, vol. 264, No. 15, pp. 8692–8698 (1989).
Stone et al. Biochemistry, vol. 25, pp. 4622–4628 (1986).
Rydel et al. Science, vol. 249, pp. 277–280 (1990).
Sakamoto et al. Peptide Chemistry, pp. 95–100 (1985).
Kobashi et al. Biochemical and Biophysical Research Communication, vol. 140, No. 1, pp. 38–42 (1986).
Taylor et al. Nucleic Acids Research, vol. 13, No. 24, pp. 8765–8785 (1985).
Kim et al. Biochemica et Biophysica Acta, vol. 872, pp. 33–41 (1986).
Kobashi et al. Archives of Biochemistry and Biophysics, vol. 245, No. 2, pp. 537–539 (1986).

*Primary Examiner*—Cecilia J. Tsang
*Assistant Examiner*—David Lukton
*Attorney, Agent, or Firm*—Birch, Stewart, Kolasch & Birch, LLP

[57] ABSTRACT

The present invention relates to hirudin variants having high anti-thrombin and anti-platelet activity, methods for producing them, and anti-coagulants having said variants as active ingredients.

Hirudin variants shown in formula (I) having tyrosine residues or having their hydroxyl group sulfated.

Methods for producing hirudin variants by sulfating hydroxyl group of said tyrosine residues, and anti-coagulants having hirudin variants shown in formula (I) as active ingredients.

Phe-Glu-A-Ile-Pro-B-Tyr(R)-Tyr(R)  (I)

[In the formula, A represents Glu or Pro, B represents Glu, Tyr (R), Glu-Asp or Glu-Tyr(R), and (R) represents the hydroxy group or its sulfated ester ($-O-SO_3H$) of tyrosine residue.]

8 Claims, 6 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..8
        ( D ) OTHER INFORMATION: /label=Formula_I
            / note= "Formula II is a specific species
            wherein residues 7 and
            8 are both tyr."

( i x ) FEATURE:
        ( A ) NAME/KEY: Modified-site
        ( B ) LOCATION: 3
        ( D ) OTHER INFORMATION: /label=variable_res
            / note= "can be either glu or pro"

( i x ) FEATURE:
        ( A ) NAME/KEY: Modified-site
        ( B ) LOCATION: 6
        ( D ) OTHER INFORMATION: /label=variable_res
            / note= "can be glu, tyr, sulfated tyr (tyr-SO3), glu-asp,
            glu-tyr or glu-tyr-SO3."

( i x ) FEATURE:
        ( A ) NAME/KEY: Modified-site
        ( B ) LOCATION: 7
        ( D ) OTHER INFORMATION: /product="can be tyr or tyr-SO3"

( i x ) FEATURE:
        ( A ) NAME/KEY: Modified-site
        ( B ) LOCATION: 8
        ( D ) OTHER INFORMATION: /product="can be tyr or tyr-SO3"

( x i ) SEQUENCE DESCRIPTION: SEQ ID NO:1:

```
Phe  Glu  Xaa  Ile  Pro  Xaa  Tyr  Tyr
 1                    5
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..12
        ( D ) OTHER INFORMATION: /label=Example_1A
            / note= "Formula 1A' shows protected intermediate made
            during synthesis of final product."

( x i ) SEQUENCE DESCRIPTION: SEQ ID NO:2:

```
Gly  Asp  Phe  Glu  Glu  Ile  Pro  Glu  Tyr  Tyr  Leu  Gln
 1              5                        10
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..12
        ( D ) OTHER INFORMATION: /label=Example_1B
        / note= "Formula 1B'shows the protected intermediate
        made during synthesis of the peptide"

( x i ) SEQUENCE DESCRIPTION: SEQ ID NO:3:

```
Gly  Asp  Phe  Glu  Glu  Ile  Pro  Tyr  Tyr  Tyr  Leu  Gln
 1              5                        10
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..12
        ( D ) OTHER INFORMATION: /label=Examples_3C-3D
        / note= "and Examples 4C-4D"

( i x ) FEATURE:
        ( A ) NAME/KEY: Modified-site
        ( B ) LOCATION: 1
        ( D ) OTHER INFORMATION: /product="succinyl-gly"

( i x ) FEATURE:
        ( A ) NAME/KEY: Modified-site
        ( B ) LOCATION: 12
        ( D ) OTHER INFORMATION: /product="gln-OH or gln-NH"

( i x ) FEATURE:
        ( A ) NAME/KEY: Modified-site
        ( B ) LOCATION: 9
        ( D ) OTHER INFORMATION: /product="tyr or tyr-SO3"

( i x ) FEATURE:
        ( A ) NAME/KEY: Modified-site
        ( B ) LOCATION: 10
        ( D ) OTHER INFORMATION: /product="tyr or tyr-SO3"

( x i ) SEQUENCE DESCRIPTION: SEQ ID NO:4:

```
Gly  Asp  Phe  Glu  Pro  Ile  Pro  Glu  Tyr  Tyr  Leu  Gln
 1              5                        10
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..12
    ( D ) OTHER INFORMATION: /label=Examples_3E_4E ( i x ) FEATURE:
    ( A ) NAME/KEY: Modified-site
    ( B ) LOCATION: 1
    ( D ) OTHER INFORMATION: /product="succinyl-gly"

( i x ) FEATURE:
    ( A ) NAME/KEY: Modified-site
    ( B ) LOCATION: 12
    ( D ) OTHER INFORMATION: /product="gln-OH"

( i x ) FEATURE:
    ( A ) NAME/KEY: Modified-site
    ( B ) LOCATION: 8
    ( D ) OTHER INFORMATION: /product="tyr or tyr-SO3"

( i x ) FEATURE:
    ( A ) NAME/KEY: Modified-site
    ( B ) LOCATION: 9
    ( D ) OTHER INFORMATION: /product="tyr or tyr-SO3"

( i x ) FEATURE:
    ( A ) NAME/KEY: Modified-site
    ( B ) LOCATION: 10
    ( D ) OTHER INFORMATION: /product="tyr or tyr-SO3"

( x i ) SEQUENCE DESCRIPTION: SEQ ID NO:5:

```
Gly  Asp  Phe  Glu  Pro  Ile  Pro  Tyr  Tyr  Tyr  Leu  Gln
 1              5                        10
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
    ( A ) NAME/KEY: Peptide
    ( B ) LOCATION: 1..11
    ( D ) OTHER INFORMATION: /label=Example_3F_4F ( i x ) FEATURE:
    ( A ) NAME/KEY: Modified-site
    ( B ) LOCATION: 1
    ( D ) OTHER INFORMATION: /product="succinyl-asp"

( i x ) FEATURE:
    ( A ) NAME/KEY: Modified-site
    ( B ) LOCATION: 11
    ( D ) OTHER INFORMATION: /product="gln-OH"

( i x ) FEATURE:
    ( A ) NAME/KEY: Modified-site
    ( B ) LOCATION: 8
    ( D ) OTHER INFORMATION: /product="tyr or tyr-SO3"

( i x ) FEATURE:
    ( A ) NAME/KEY: Modified-site
    ( B ) LOCATION: 9
    ( D ) OTHER INFORMATION: /product="tyr or tyr-SO3"

( x i ) SEQUENCE DESCRIPTION: SEQ ID NO:6:

Asp Phe Glu Pro Ile Pro Glu Tyr Tyr Leu Gln
 1           5                    10

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..10
        ( D ) OTHER INFORMATION: /label=Example_3G_4G ( i x ) FEATURE:
        ( A ) NAME/KEY: Modified-site
        ( B ) LOCATION: 1
        ( D ) OTHER INFORMATION: /product="succinyl-phe"

( i x ) FEATURE:
        ( A ) NAME/KEY: Modified-site
        ( B ) LOCATION: 10
        ( D ) OTHER INFORMATION: /product="gln-OH"

( i x ) FEATURE:
        ( A ) NAME/KEY: Modified-site
        ( B ) LOCATION: 7
        ( D ) OTHER INFORMATION: /product="tyr or tyr-SO3"

( i x ) FEATURE:
        ( A ) NAME/KEY: Modified-site
        ( B ) LOCATION: 8
        ( D ) OTHER INFORMATION: /product="tyr or tyr-SO3"

( x i ) SEQUENCE DESCRIPTION: SEQ ID NO:7:

Phe Glu Pro Ile Pro Glu Tyr Tyr Leu Gln
 1           5                    10

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( i x ) FEATURE:
        ( A ) NAME/KEY: Peptide
        ( B ) LOCATION: 1..9
        ( D ) OTHER INFORMATION: /label=Example_3H_4H ( i x ) FEATURE:
        ( A ) NAME/KEY: Modified-site
        ( B ) LOCATION: 1
        ( D ) OTHER INFORMATION: /product="succinyl-glu"

( i x ) FEATURE:
        ( A ) NAME/KEY: Modified-site
        ( B ) LOCATION: 9
        ( D ) OTHER INFORMATION: /product="gln-OH"

( i x ) FEATURE:
        ( A ) NAME/KEY: Modified-site
        ( B ) LOCATION: 6
        ( D ) OTHER INFORMATION: /product="tyr or tyr-SO3"

( i x ) FEATURE:

(A) NAME/KEY: Modified-site
                    (B) LOCATION: 7
                    (D) OTHER INFORMATION: /product="tyr or tyr-SO3"

(xi) SEQUENCE DESCRIPTION: SEQ ID NO:8:

Glu  Pro  Ile  Pro  Glu  Tyr  Tyr  Leu  Gln
        1                     5

(2) INFORMATION FOR SEQ ID NO:9:

(i) SEQUENCE CHARACTERISTICS:
                    (A) LENGTH: 8 amino acids
                    (B) TYPE: amino acid
                    (C) STRANDEDNESS: Not Relevant
                    (D) TOPOLOGY: linear (ii) MOLECULE TYPE: peptide (v) FRAGMENT TYPE: internal (ix) FEATURE:
                    (A) NAME/KEY: Modified-site
                    (B) LOCATION: 1
                    (D) OTHER INFORMATION: /product="succinyl-phe"

(ix) FEATURE:
                    (A) NAME/KEY: Modified-site
                    (B) LOCATION: 7
                    (D) OTHER INFORMATION: /product="tyr or tyr-SO3"

(ix) FEATURE:
                    (A) NAME/KEY: Modified-site
                    (B) LOCATION: 8
                    (D) OTHER INFORMATION: /product="variously modified tyr"
                            / note= "tyr-OH, tyr-NH2, tyr-NH(CH2)2COOH,
                            tyr- NH(CH2)4COOH, tyr-Tau-NH2, tyr-NH(CH2)3OH or
                            tyr- (L)Asu(OMe)OMe."

(ix) FEATURE:
                    (A) NAME/KEY: Peptide
                    (B) LOCATION: 1..8
                    (D) OTHER INFORMATION: /label=Examples_51-60
                            / note= "formulae (i-viii) are the protected peptide
                            intermediates used to make the peptides of Examples
                            5 and 6"

(xi) SEQUENCE DESCRIPTION: SEQ ID NO:9:

Phe  Glu  Pro  Ile  Pro  Glu  Tyr  Tyr
        1                     5

(2) INFORMATION FOR SEQ ID NO:10:

(i) SEQUENCE CHARACTERISTICS:
                    (A) LENGTH: 9 amino acids
                    (B) TYPE: amino acid
                    (C) STRANDEDNESS: Not Relevant
                    (D) TOPOLOGY: linear (ii) MOLECULE TYPE: peptide (v) FRAGMENT TYPE: internal (ix) FEATURE:
                    (A) NAME/KEY: Peptide
                    (B) LOCATION: 1..9
                    (D) OTHER INFORMATION: /label=Examples_7P-8Y
                            / note= "formulae (x-xxi) are the protected intermediates
                            used in making the peptides of Examples 7 and 8."

(ix) FEATURE:
                    (A) NAME/KEY: Modified-site
                    (B) LOCATION: 1
                    (D) OTHER INFORMATION: /product="succinyl-phe"

(ix) FEATURE:
                    (A) NAME/KEY: Modified-site (B) LOCATION: 7
(D) OTHER INFORMATION: /product="tyr or tyr-SO3"

(ix) FEATURE:
(A) NAME/KEY: Modified-site
(B) LOCATION: 8
(D) OTHER INFORMATION: /product="tyr or tyr-SO3"

(ix) FEATURE:
(A) NAME/KEY: Modified-site
(B) LOCATION: 9
(D) OTHER INFORMATION: /product="variously modified
    leucine"
/ note= "leu-ol, leu-OH, leu-NHEt, leu-Tau-NH2,
leu-(D)glu- OH, leu-(D)Asu(OMe)OMe, leu-(L)Asu(OMe)OMe,
leu- (D)Asu(NH2)NH2, leu-(L)Asu(NH2)NH2) or
leu- NHPO(OH)2"

(xi) SEQUENCE DESCRIPTION: SEQ ID NO:10:

Phe Glu Pro Ile Pro Glu Tyr Tyr Leu
1               5

(2) INFORMATION FOR SEQ ID NO:11:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide formula
(III)"

(xi) SEQUENCE DESCRIPTION: SEQ ID NO:11:

GAAATCCCGT ACTACTACCT GCAG                                          24

(2) INFORMATION FOR SEQ ID NO:12:

(i) SEQUENCE CHARACTERISTICS:
(A) LENGTH: 65 amino acids
(B) TYPE: amino acid
(C) STRANDEDNESS: Not Relevant
(D) TOPOLOGY: linear (ii) MOLECULE TYPE: protein (v) FRAGMENT TYPE: internal (ix) FEATURE:
(A) NAME/KEY: Protein
(B) LOCATION: 1..65
(D) OTHER INFORMATION: /label=variant_hirudin
    / note= "HV-17"

(ix) FEATURE:
(A) NAME/KEY: Modified-site
(B) LOCATION: 62
(D) OTHER INFORMATION: /product="tyr or tyr-SO3"

(ix) FEATURE:
(A) NAME/KEY: Modified-site
(B) LOCATION: 63
(D) OTHER INFORMATION: /product="tyr or tyr-SO3"

(xi) SEQUENCE DESCRIPTION: SEQ ID NO:12:

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

```
            Gln Ser His Asn Asp Gly Asp Phe Glu Glu Ile Pro Tyr Tyr Tyr Leu
                50                  55                  60

Gln
            65
```

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: C-terminal ( i x ) FEATURE:
        ( A ) NAME/KEY: Peptide
        ( B ) LOCATION: 1..12
        ( D ) OTHER INFORMATION: /note= "HV-1 (54-65)"

( i x ) FEATURE:
        ( A ) NAME/KEY: Modified-site
        ( B ) LOCATION: 1
        ( D ) OTHER INFORMATION: /product="H-gly"

( i x ) FEATURE:
        ( A ) NAME/KEY: Modified-site
        ( B ) LOCATION: 12
        ( D ) OTHER INFORMATION: /product="gln-OH"

( x i ) SEQUENCE DESCRIPTION: SEQ ID NO:13:

```
            Gly Asp Phe Glu Glu Ile Pro Glu Glu Tyr Leu Gln
            1               5                   10
```

( 2 ) INFORMATION FOR SEQ ID NO:14:

( i ) SEQUENCE CHARACTERISTICS:
        ( A ) LENGTH: 65 amino acids
        ( B ) TYPE: amino acid
        ( C ) STRANDEDNESS: Not Relevant
        ( D ) TOPOLOGY: linear ( i i ) MOLECULE TYPE: protein ( v ) FRAGMENT TYPE: internal ( i x ) FEATURE:
        ( A ) NAME/KEY: Protein
        ( B ) LOCATION: 1..65
        ( D ) OTHER INFORMATION: /note= "hirudin HV-1"

( x i ) SEQUENCE DESCRIPTION: SEQ ID NO:14:

```
            Val Val Tyr Thr Asp Cys Thr Glu Ser Gly Gln Asn Leu Cys Leu Cys
            1               5                   10                  15

Glu Gly Ser Asn Val Cys Gly Gln Gly Asn Lys Cys Ile Leu Gly Ser
                            20                  25                  30

Asp Gly Glu Lys Asn Gln Cys Val Thr Gly Glu Gly Thr Pro Lys Pro
                        35                  40                  45

Gln Ser His Asn Asp Gly Asp Phe Glu Glu Ile Pro Glu Glu Tyr Leu
                50                  55                  60

Gln
            65
```

( 2 ) INFORMATION FOR SEQ ID NO:15:

( i ) SEQUENCE CHARACTERISTICS:

(A) LENGTH: 55 amino acids
(B) TYPE: amino acid
(C) STRANDEDNESS: Not Relevant
(D) TOPOLOGY: linear (i i) MOLECULE TYPE: protein (v) FRAGMENT TYPE: N-terminal (i x) FEATURE:
(A) NAME/KEY: Protein
(B) LOCATION: 1..55
(D) OTHER INFORMATION: /note= "Amino-terminal 55 residues of hirudin HV-2"

(x i) SEQUENCE DESCRIPTION: SEQ ID NO:15:

| Ile | Thr | Tyr | Thr | Asp | Cys | Thr | Glu | Ser | Gly | Gln | Asn | Leu | Cys | Leu | Cys |
|-----|-----|-----|-----|-----|-----|-----|-----|-----|-----|-----|-----|-----|-----|-----|-----|
| 1 | | | | 5 | | | | | 10 | | | | | 15 | |
| Glu | Gly | Ser | Asn | Val | Cys | Gly | Lys | Gly | Asn | Lys | Cys | Ile | Leu | Gly | Ser |
| | | | 20 | | | | 25 | | | | | | 30 | | |
| Asn | Gly | Lys | Gly | Asn | Gln | Cys | Val | Thr | Gly | Glu | Gly | Thr | Pro | Asn | Pro |
| | | 35 | | | | | 40 | | | | | 45 | | | |
| Glu | Ser | His | Asn | Asn | Gly | Asp | | | | | | | | | |
| | 50 | | | | | 55 | | | | | | | | | |

(2) INFORMATION FOR SEQ ID NO:16:

(i) SEQUENCE CHARACTERISTICS:
(A) LENGTH: 55 amino acids
(B) TYPE: amino acid
(C) STRANDEDNESS: Not Relevant
(D) TOPOLOGY: linear (i i) MOLECULE TYPE: protein (v) FRAGMENT TYPE: N-terminal (i x) FEATURE:
(A) NAME/KEY: Protein
(B) LOCATION: 1..55
(D) OTHER INFORMATION: /note= "Amino terminal 55 residues of hirudin HV-3"

(x i) SEQUENCE DESCRIPTION: SEQ ID NO:16:

| Ile | Thr | Tyr | Thr | Asp | Cys | Thr | Glu | Ser | Gly | Gln | Asn | Leu | Cys | Leu | Cys |
|-----|-----|-----|-----|-----|-----|-----|-----|-----|-----|-----|-----|-----|-----|-----|-----|
| 1 | | | | 5 | | | | | 10 | | | | | 15 | |
| Glu | Gly | Ser | Asn | Val | Cys | Gly | Lys | Gly | Asn | Lys | Cys | Ile | Leu | Gly | Ser |
| | | | 20 | | | | 25 | | | | | | 30 | | |
| Gln | Gly | Lys | Asp | Asn | Gln | Cys | Val | Thr | Gly | Glu | Gly | Thr | Pro | Lys | Pro |
| | | 35 | | | | | 40 | | | | | 45 | | | |
| Gln | Ser | His | Asn | Gln | Gly | Asp | | | | | | | | | |
| | 50 | | | | | 55 | | | | | | | | | |

ANTICOAGULANT HIRUDIN VARIANTS AND METHODS FOR THEIR PRODUCTION

This application is a continuation of application Ser. No. 07/946,303, filed as PCT/JP92/00253 filed Mar. 4, 1992, now abandoned.

TECHNICAL FIELD

The present invention relates to hirudin variants or their salts, methods for their production and anti-coagulants having said compounds as active ingredients. The hirudin variants or their salts in the present invention are useful as drugs for pharmacological therapy of acute deep venous thrombosis, pulmonary thromboembolism, acute arterial embolism of limbs, myocardial infarction and intravascular coagulation on infection.

BACKGROUND ART

Natural hirudin is a mixture of peptides composed of 65 or 66 amino acids and is secreted from salivary glands of medicinal leeches in very small amounts. A variant called HV-1 is the first hirudin isolated from leeches. A variant called HV-2 differs from the aforesaid HV-1 in 9 amino acids, and HV-3 is identical with HV-2 up to the 32nd serine and differs in 10 amino acids including an additional 63rd alanine on the C-terminal end.

Further, the existence of tyrosine in which the phenolic hydroxide residue is sulfated as shown in the following formula

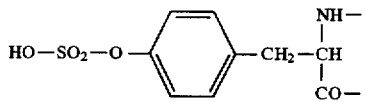

or —[Tyr($SO_3H$)]— has been confirmed.

It has been reported that the anti-thrombin activity increases about 10 times by existence of the sulfate on the tyrosine residue.

So far, it is very difficult to manufacture polypeptides having sulfated tyrosine in the molecule. When chemical introduction of a sulfate group on the tyrosine residue in polypeptide obtained by methods such as recombinant DNA technology is considered, in which case the amino acid sequence is long, it is very difficult to sulfate targeted tyrosine selectively without influencing other amino acids. It also requires drastic reaction conditions which often cause disruption of peptide bonds and it is difficult to obtain the sulfated compound in satisfactory yield. For this reason, hirudins under development at present as anti-coagulants are non-sulfated ones and have low activities.

Although the therapeutic application of hirudin as an anti-coagulant is thought to be effective, being a foreign compound, allergic symptom such as shock and eczema are possible. However, it is thought to be possible to reduce allergic responses by decreasing the administration dose or shortening the amino acid sequence of the polypeptide. The aim of the present invention is to provide hirudin variants with higher anti-thrombin activity by sulfating the hydroxyl group of tyrosine residue in the molecule.

DISCLOSURE OF INVENTION

The present invention relates to hirudin variants or their salts having the following amino acid sequence in formula (I) (SEQ. ID. NO:1) as a part of their sequence or as all of their sequence.

Phe-Glu-A-Ile-Pro-B-Tyr(R)-Tyr(R)     (I)

In the formula, A represents Glu or Pro, B represents Glu, Tyr(R), Glu-Asp or Glu-Tyr(R), and (R) represents the hydroxy group or its sulfated ester (—O—$SO_3H$) of the tyrosine residue.

Further, the present invention relates to the method of manufacturing of the hirudin variants or their salts characterized by sulfating the hydroxyl group of the tyrosine residue in the amino acid sequence of hirudin variants or their salts having the following formula (II) SEQ. ID. NO:1 as a part or as all of the amino acid sequence.

Phe-Glu-A-Ile-Pro-B-Tyr-Tyr     (II)

In the formula, A represents Glu or Pro, and B represents Glu, Tyr, Glu-Asp or Glu-Tyr, respectively.

The sulfation in the present invention maybe carried out by reacting hirudin variants or their salts with aryl sulfotransferase in the presence of sulfate group donors, with sulfur trioxide complex, or with sulfuric acid and dicyclohexylcarbodiimide One of the important points of the present invention is that the recognition activity against tyrosine by aryl sulfotransferase is improved by substituting 1 or 2 amino acids adjacent to the tyrosine residue in the C terminal of natural hirudin to tyrosine. With the polypeptides used in the present invention, the present inventors have confirmed that the sulfation reaction by aryl sulfotransferase will hardly take effect without the aforesaid treatment.

Another important point of the present invention is, if a peptide contains a sequence of 8 amino acids starting from the 56th amino acid from the N-terminal to the C-terminal of natural hirudin, or if it is composed solely aforesaid sequence of 8 amino acids, or if both ends of it are substituted by a protecting group such as a succinyl group or an amino group, it should show a high anti-thrombin activity as long as it is sulfated. Particularly, a compound composed of only 8 amino acids according to formula (I), having the N-terminal protected by a succinyl group and two tyrosine residues sulfated in both hydroxyl group thereof, is confirmed to have an extremely high anti-thrombin activity.

The hirudin variants in the present invention are the peptides having aforesaid amino acid sequence and having the high anti-thrombin activity.

The C-terminal of the compounds in the present invention are the abovementioned -Tyr(R), -Tyr(R)-Leu or -Tyr(R)-Asp. Further, the aforesaid -Tyr(R), -Tyr(R)-Len or -Tyr(R)-Asp mayhave the following substituents.

Amide, lower alkyl($C_1$–$C_5$) amide, [e.g. —$NHCH_3$, —$NHC_2H_5$], amino acids [e.g. natural amino acids, D-Glu, α-amino adipic acid, α-amino suberic acid(Asu)], lower alkyl($C_1$–$C_5$) ester of amino acids [e.g. Glu—$OC_2H_5$, Glu ($OC_2H_5$)$OC_2H_5$, Asu (OMe)—OMe], amino acid amnide [e.g. Glu—$NH_2$, —Gln—$NH_2$, Asu($NH_2$)$NH_2$], lower alkyl ($C_1$–$C_5$) amide of amino acids [e.g. Glu—$NHC_2H_5$, —Gln—$NHC_2H_5$], amino sulfonic acids [e.g. —NH—$CH_2$—$SO_3H$, taulin (Tau), —NH—($CH_2$)$_3$—$SO_3H$], aminosulfone amide [e.g. —NH—$CH_2$—$SO_2NH_2$, Tau—$NH_2$], amino alcohol [e.g. —NH($CH_2$)$_2$—OH, —NH($CH_2$)$_3$—OH, Leu—ol], amino phosphoric acid [e.g. —NHPO(OH)$_3$], amino phosphoric acid ester [e.g. —NHPO($OC_2H_5$)$_3$, —NHPO(OPh)$_2$] or amino phosphone amide [e.g. —NHPO—($NH_2$)$_2$].

The following acyl group may be used as protecting groups of the N-terminal amino group:

Alkanoyl [e.g. acetyl($CH_3CO$—), butyryl ($CH_3CH_2CH_2CO$—), isobutyryl (($CH_3$)$_2$CHCO—)], substitutedalkanoyl [e.g.lactinyl(CH$_3$CH(OH)CO—)], carboxy alkanoyl [e.g.succinyl(HOOCCH$_2$CH$_2$CO—), glutaryl (HOOC(CH$_2$)$_3$CO—)], substituted carboxy alkanoyl [e.g. malicyl (HOOCCH(OH)CH$_2$CO—)], alkoxycarbonyl alkanoyl [e.g. ethoxy carbonyl propionyl (EtOOCCH $_2$CH$_2$CO—)], carbamoyl alkanoyl [e.g.carbamoyl propionyl (H$_2$NOCCH$_2$CH$_2$CO—)], alkenoyl [e.g.acryl (CH$_2$=CHCO—), oleonyl (CH$_3$(CH$_2$)$_7$CH=CH(CH$_2$)$_7$CO—)], carboxy alkenoyl [e.g. 3-carboxy-cis-propenoyl, 3-carboxy-trans-propenoyl (HOOCCH=CHCO—)], alkoxycarbonyl alkenoyl [e.g.ethoxy carbonyl acryloyl EtOOCCH=CHCO—)], or carbamoylalkenoyl [e.g. carbamoylacryloyl (H$_2$NOCCH=CHCO—)]

The hirudin variants of the present invention may form salts with acids or bases etc.

Salts in the present invention may be the following:

hydrochloride,sulfate, p-toluene sulfonate, phosphate, formic acid salt, malonic acid salt, succinic acid salt, lactic acid salt, oxalic acid salt, tartaric acid salt, acetic acid salt, trifluoroacetic acid salt, sodium salt, potassium salt, magnesium salt, barium salt, calcium salt, ammonium salt, piperidine salt, morpholine salt, dimethyl amine salt, diethyl amine salt, etc.

A preferred genus of peptides in accordance with the present invention is represented by the following formula:

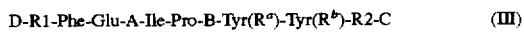

D-R1-Phe-Glu-A-Ile-Pro-B-Tyr(R$^a$)-Tyr(R$^b$)-R2-C     (III)

wherein the peptide has an amino acid sequence consisting of 12 amino acids or less;

A is Glu or Pro;

B is Glu, Tyr or Tyr (SO$_3$H);

Tyr(R$^a$) and Tyr(R$^b$) are independently selected from Tyr and Tyr (SO$_3$H);

Tyr (SO$_3$H) is a sulfated ester of tyrosine;

R1 is -Gly-Asp-, -Asp-, or a bond;

preferably at least one of B, Tyr(R$^a$) and Tyr(R$^b$) is Tyr (SO$_3$H);

D is bonded to the N-terminal amino group of R1 and is selected from the group consisting of a hydrogen atom, an alkanoyl group, an alkanoyl group bearing an OH group, a carboxyalkanoyl group, a carboxyalkanoyl group bearing an OH group, an alkoxycarbonyl alkanoyl group, an alkenoyl group, a carboxyalkenoyl group, an alkoxycarbonyl alkenoyl group, and a carbamoylalkenoyl group;

R2 is optionally present and is Leu or Asp; and

C optionally replaces the C-terminal hydroxyl of the peptide and is selected from the group consisting of an —NH$_2$ group, a (C$_1$–C$_5$-alkyl)amino group, an amino acid, a C$_1$–C$_5$ alkyl ester of an amino acid, an amino acid amide group, a (C$_1$–C$_5$-alkyl)amide of an amino acid, an amino sulfonic acid group, an aminosulfonamide group, an amino alcohol group, an amino phosphoric acid group, an amino phosphoric acid ester, and an aminophosphonamide group.

The polypeptides including the amino acid sequence shown in aforementioned formula (II) can easily be produced by various known methods. Such methods include chemical synthesis methods like the solid phase method and the liquid phase method, recombinant DNA method and the combination of these methods.

The method of sulfation using aryl sulfotransferase in the present invention has the advantage that it can sulfate tyrosine residues specifically in polypeptides of long amino acid sequence under mild condition so that it does not affect other amino acids. There is no particular limitation to the enzyme used for the sulfation as long as it has aryl sulfotransferase activity, for instance, the one derived from human enterobacteria (Eubacterium A-44).

Preferable examples of sulfate group donors are aryl sulfates or their salts, for example, phenyl sulfate, p- or m-nitro phenyl sulfate, p- or m- acetyl phenyl sulfate, tyramine sulfate, p-nitro catechol sulfate, p-nitro catechol disulfate, pico sulfate, phenolphthalein disulfate, 4-methyl unberiferril sulfate, 1- or 2-naphthyl sulfate, 4-nitro-l-naphthyl sulfate, 4-fenantoryl sulfate, or their alkali metal salts.

Reaction temperature and pH should be optimized depending on the nature of the polypeptide and ayl sulfotransferase; however, the present inventors have found preferable conditions at the temperature of 25–37 ° C. and at the pH of 8–9.

When the reaction is over, the sulfated compound may easily be separated and collected from unreacted materials by high performance liquid chromatography under appropriate conditions. Recovered unreacted materials may be re-used for sulfation of the polypeptide by feeding them back to the reaction system.

On the other hand, those polypeptide chains of relatively short amino acids including the amino acid sequence shown in aforementioned formula (I) may be generally chemically synthesized by solid phase or liquid phase methods. The hydroxyl group of the tyrosine residue of these peptides may be sulfated by chemical methods using sulfating reagents. The sulfation may be carried out by treating the aforementioned polypeptide chain at around room temperature, in the presence of solvents, such as pyridine or dimethyl formamide, with a 10–500 equivalent amount excess of sulfur trioxide complex, such as pyridine-sulfur trioxide, dioxane-sulfur trioxide, trimethylamine-sulfur trioxide, triethylamine-sulfur trioxide, dimethylaniline-sulfur trioxide, thioxane-sulfur trioxide, bis (2-chloroethyl)ether-sulfur trioxide and, 2-methylpiridine-sulfur trioxide, quinoline-sulfur trioxide, dimethylformamide-sulfur trioxide. As an alternative method, sulfation may be done by condensation by treating an excess of sulfuric acid and dicyclohexylcarbodiimide with the aforementioned polypeptide chain at around room temperature.

When compounds obtained in the present invention are going to be used as pharmaceuticals, for example, they may be administered orally, or subcutaneously, intravenously, intramuscularly, or intraarterially by injection, or non-orally through mucous membranes. The dose of 0.1–1000 mg for an adult per a day is suitable. The total amount may be administered one to several times. However, naturally, the amount may be properly increased or decreased upon necessity. For oral administration, they may be used in form of a tablet, capsule or granule, which are prepared by using pharmaceutically acceptable additives, diluents, carrier, excipients, etc. For non-oral administration, the compounds may be prepared in injectable formulations of solutions or suspensions, using sterilized solutions of water or oils, detergents, other pharmaceutically acceptable additives, pharmacologically acceptable diluents or carriers, etc. Similarly, using pharmaceutically acceptable additives, diluents, carriers or excipients etc., the compounds maybe prepared in suppository form or a into formulation that enables absorption through the skin or mucous membranes.

In the FIGS. A and B stands for peptide(A) and peptide (B), respectively.

BEST MODE FOR CARRYING OUT THE INVENTION

Example 1
Production of
(A) Gly-Asp-Ple-Glu-Glu-Ile-Pro-Glu-Tyr-Tyr-Leu-Glin, SEQ. ID. NO:2 and
(B) Gly-Asp-Phe-Glu-Glu-Ile-Pro-Tyr-Tyr-Tyr-Leu-Gln SEQ. ID. NO:3

Above mentioned peptides (A) and (B) were synthesized by solid phase peptide synthesizer 430A of the Applied Biosystems. After deprotection of Boc group of the starting material Boc-Gln-OCH$_2$-PAM resin (0.5 mM) by trifluoroacetate, peptide chain elongation was done by condensation of amino acids in order from the C-terminal by the symmetrical anhydride method. Thus, the following protected peptides (A') and (B'), as shown in the following formula, bound to resin were obtained.

(A') Gly-Asp(OBzl)-Phe-Glu(OBzl)-Glu(OBzl)-Iie-Pro-Glu(OBzl)-Tyr(Br—Z)-Tyr(Br—Z)-Leu-Gln—OCH$_2$-resin (B') Gly-Asp(OBzl)-Phe-Glu(OBzl)-Glu(OBzl)-Ile-Pro-Tyr(Br—Z)-Tyr(Br—Z)-Tyr(Br—Z)-Leu-Gln-OCH$_2$-resin 0.75 g of both resins having the protected peptide bound were treated with 17 ml of hydrogen fluoride anhydride in the presence of 1.9 ml of anisole at 0° C. for 1 hour to completely deprotect all the protection groups. After the deprotection, hydrogen fluoride was vaporized off, followed by washing of the residue with diethyl ether and drying with nitrogen gas. After dissolving in 100 ml of 1N acetic acid and removing the resin by filtration, they were loaded on an anion exchange column (DOWEX 1-X2) followed by elution of peptides by acetic acid. Next, they were purified by high performance liquid chromatography (HPLC) under the following condition.

| Equipment: | Waters Delta Prep 3000 |
|---|---|
| Column: | Preppack C$_{18}$, 300 Å |
| Running buffer: | A. 0.05% trifluoroacetate/water |
| | B. acetonitrile |
| Gradient: | B. 0-100%/100 min. |
| Flow rate: | 80 ml/min. |
| Detection: | 214 nm |

Elution time of peptide (A) was 32 minutes and of peptide (B) was 31 minutes. Then, after removing acetonitrile in the process of concentration, lyophilization was done. Here, the following is the result of amino acid analysis of (A) and (B), respectively, when these peptides were hydrolysed in 6N hydrochloric acid at 110° C. for 24 hours.

| amino acid | (A) | (B) |
|---|---|---|
| Asx | 1.03 (1) | 1.01 (1) |
| Glx | 4.37 (4) | 3.24 (3) |
| Gly | 1.00 (1) | 1.00 (1) |
| Ile | 1.00 (1) | 0.99 (1) |
| Leu | 1.06 (1) | 1.05 (1) |
| Tyr | 2.07 (2) | 3.09 (3) |
| Phe | 1.03 (1) | 1.02 (1) |
| Pro | 1.02 (1) | 1.01 (1) |

Figures in parenthesis show the theoretical value

Figure 1A:
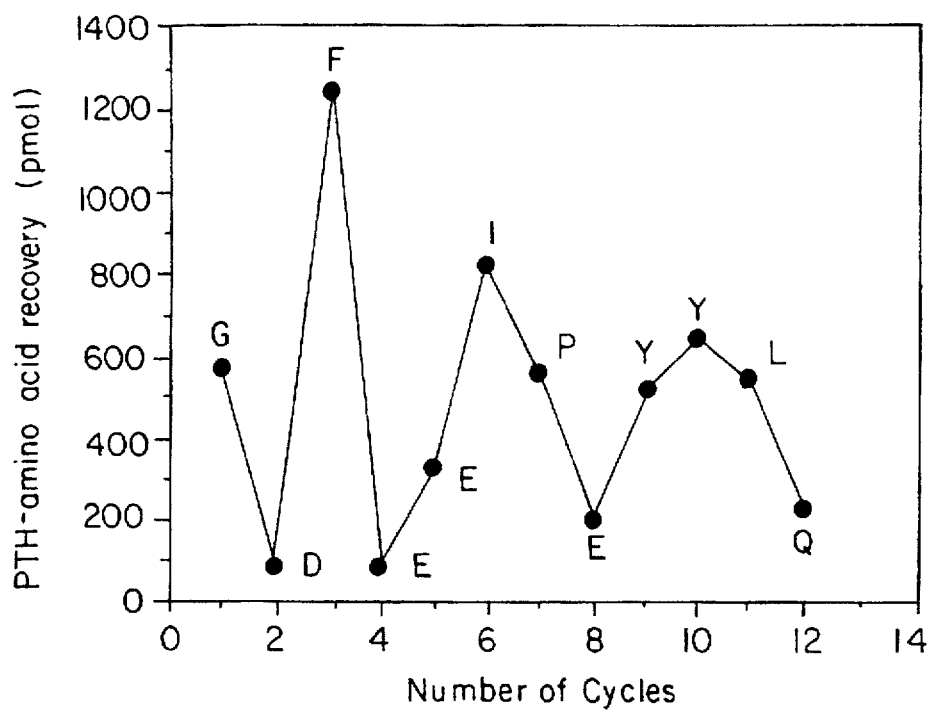
FIGS. 1A–1B show the relation of recovery of amino acids synthesized in example 1 and their phenylthiohydantoin(PTH) derivatives.
Figure 1B:
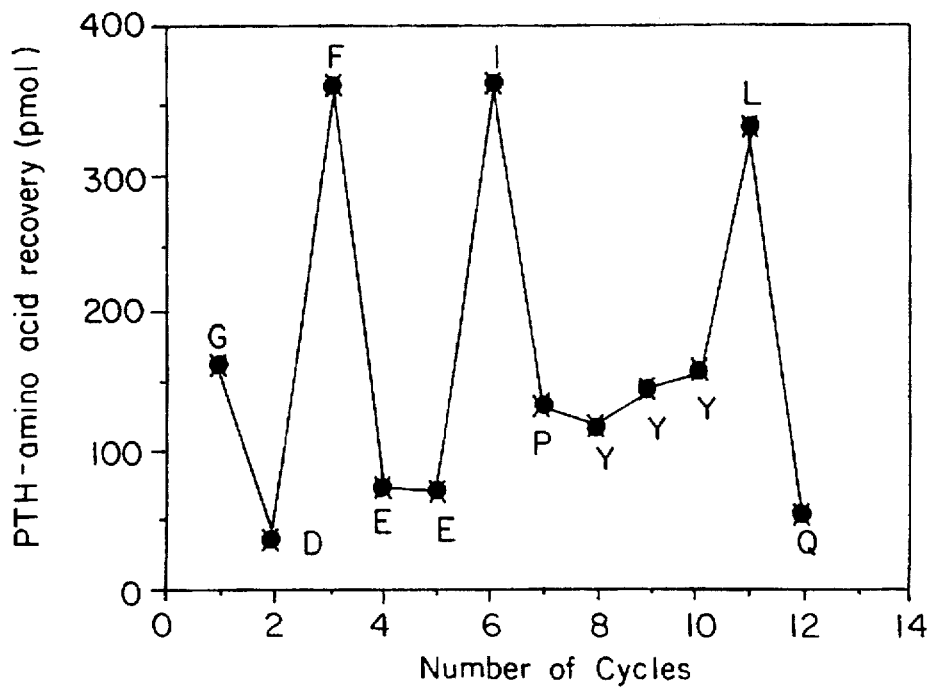

The sequence of aforementioned peptides (A) and (B) were confirmed by a gas phase sequencer (Applied Biosystems 477 A). The relation of identified amino acid and recovery of phenylthiohydantoin (PTH) derivative is shown in FIG. 1.

Figure 2A:
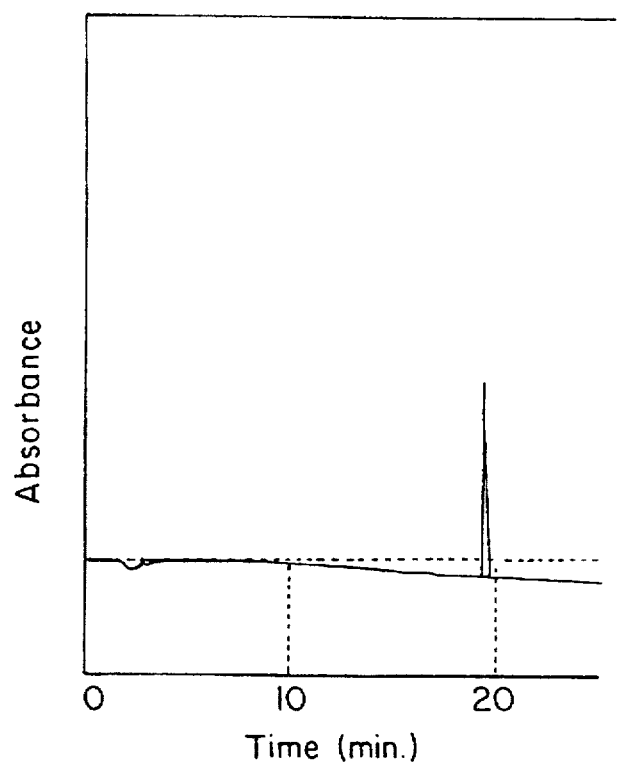
FIG. 2A-2B show the profile of HPLC analysis of each peptide synthesized in example 1.
Figure 2B:
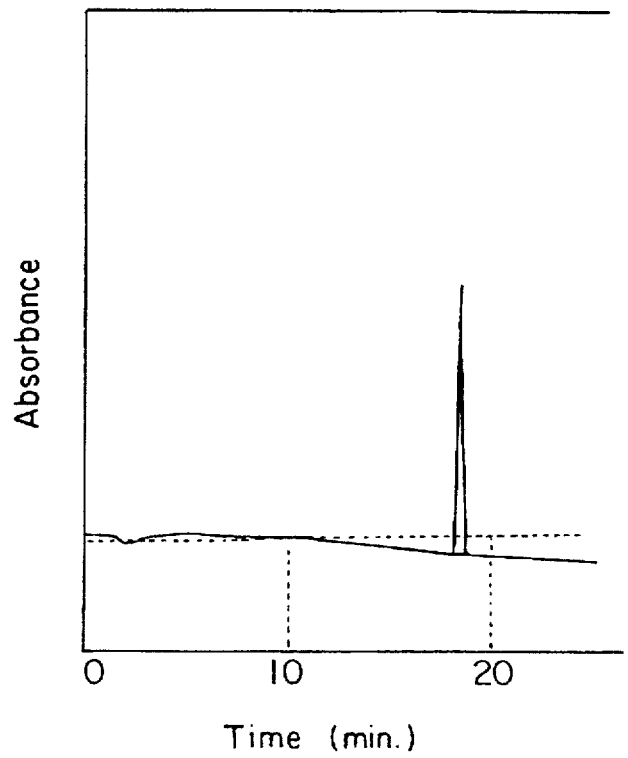

The purity of aforementioned peptides (A) and (B) were both over 99% when analyzed by HPLC [Waters, µ-Bondapak C18 (3.9×150 mm)]. The profiles of HPLC analysis of each peptide are shown in FIG. 2.

Example 2
Production of sulfated form of
(A) Glv-Asp-Phe-Glu-Glu-Ie-Pro-Glu-Tyr-Tyr-Leu-Gln, SEQ. ID. NO:2 and
(B) Gly-Asp-Phe-Glu-Glu-Ile-Pro-Tyr-Tyr-Tyr-Leu-Gln SEQ. ID. NO:3

Sulfation of peptides (A) and (B) synthesized in Example 1 was done using aryl sulfotransferase, derived from human enterobacteria under the following conditions.

| Peptide: | 0.1 mM |
|---|---|
| p-nitrophenylsulfate: | 1.0 mM |
| Sulfotransferase: | 10 U/ml |
| Magnesium chloride: | 25 mM |
| Reaction buffer: | 0.1M Tris-hydrochloride buffer (pH 8.6) |
| Reaction temperature: | 37° C. |
| Reaction time: | 66-96 hours |

Separation and collection of sulfated compounds were done by HPLC under the following conditions.

| Column: | Waters µ-Bondapak C$_{18}$ (3.9 × 150 mm) |
|---|---|
| Running buffer: | A. 0.1% trifluoro acetate/water |
| | B. acetonitrile |
| Gradient: | B. 10-60%/50 min. |
| Flow rate: | 1.5 ml/min. |
| Detection: | 230 nm |

Under the condition, sulfated peptide (A) eluted at 23.3 minutes, and three kinds of sulfated peptide (B) eluted at 21.4 minutes, 23.4 minutes and 24.6 minutes respectively. Each fraction of sulfated compound was lyophilized after removing acetonitrile in the process of concentration.

Figure 3B:
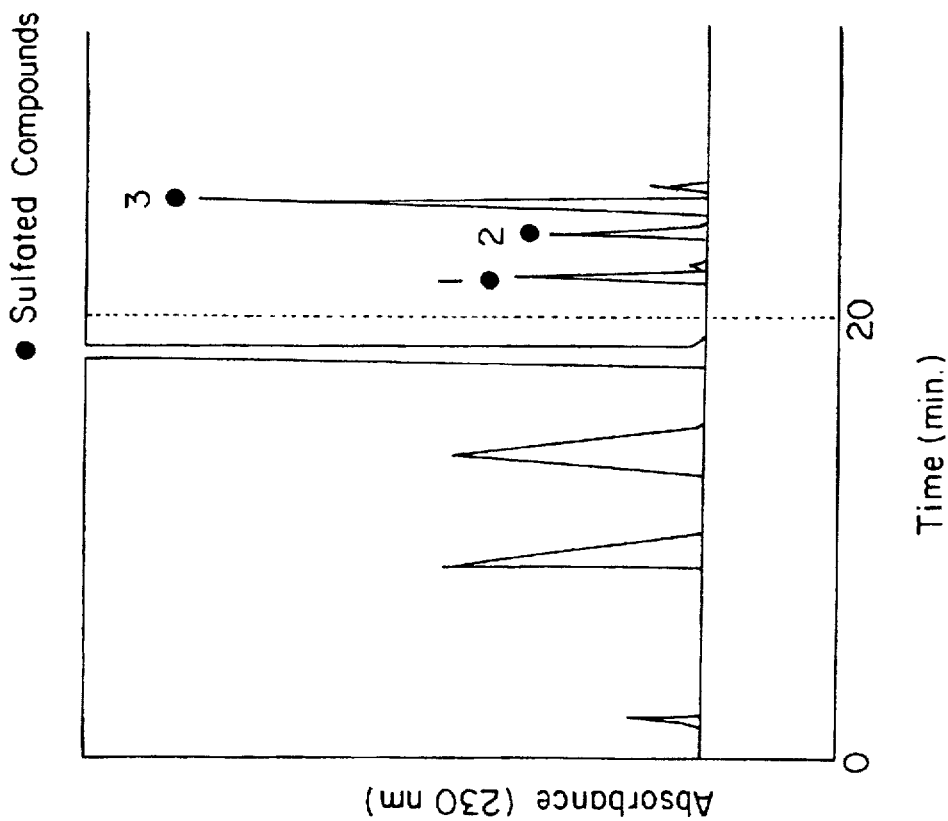
FIGS. 3A-3B show profile of HPLC analysis chromatogram of sulfated compound described in example 2.
Figure 3A:
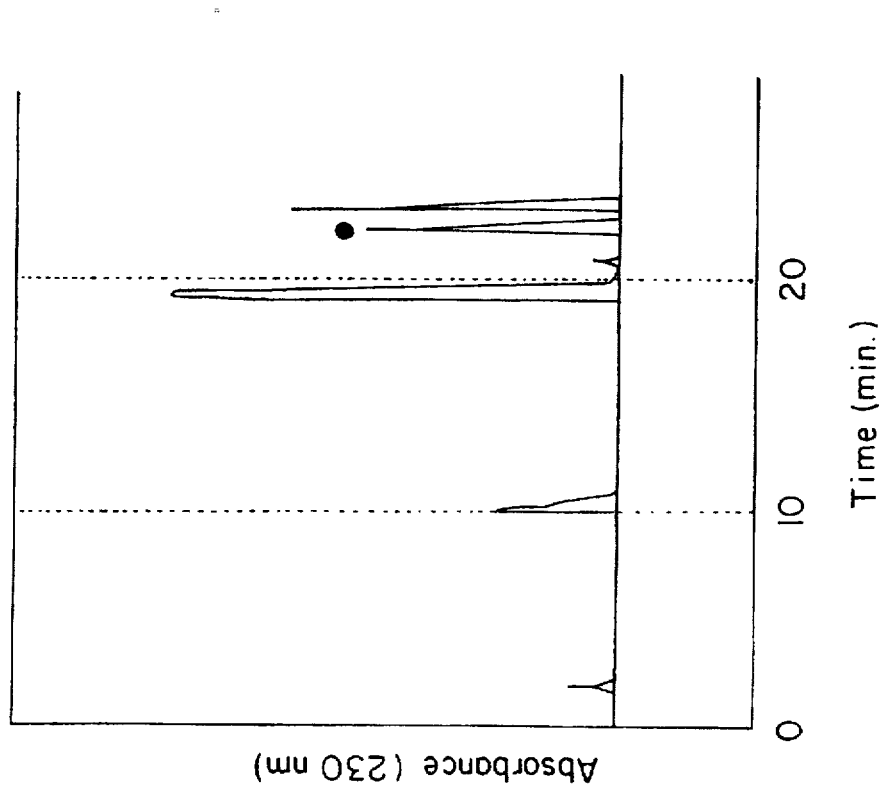

Profiles of HPLC analysis of each peptide, sulfated enzymatically under the abovementioned conditions, are shown in FIG. 3 (A) and (B), respectively.

Identification of sulfated site

The identification of the sulfated site of aforesaid sulfated peptides (A) and (B) was done by using aminopeptidase M, carboxypeptidase Y, chymotrypsin and V8 protease.

Figure 4:
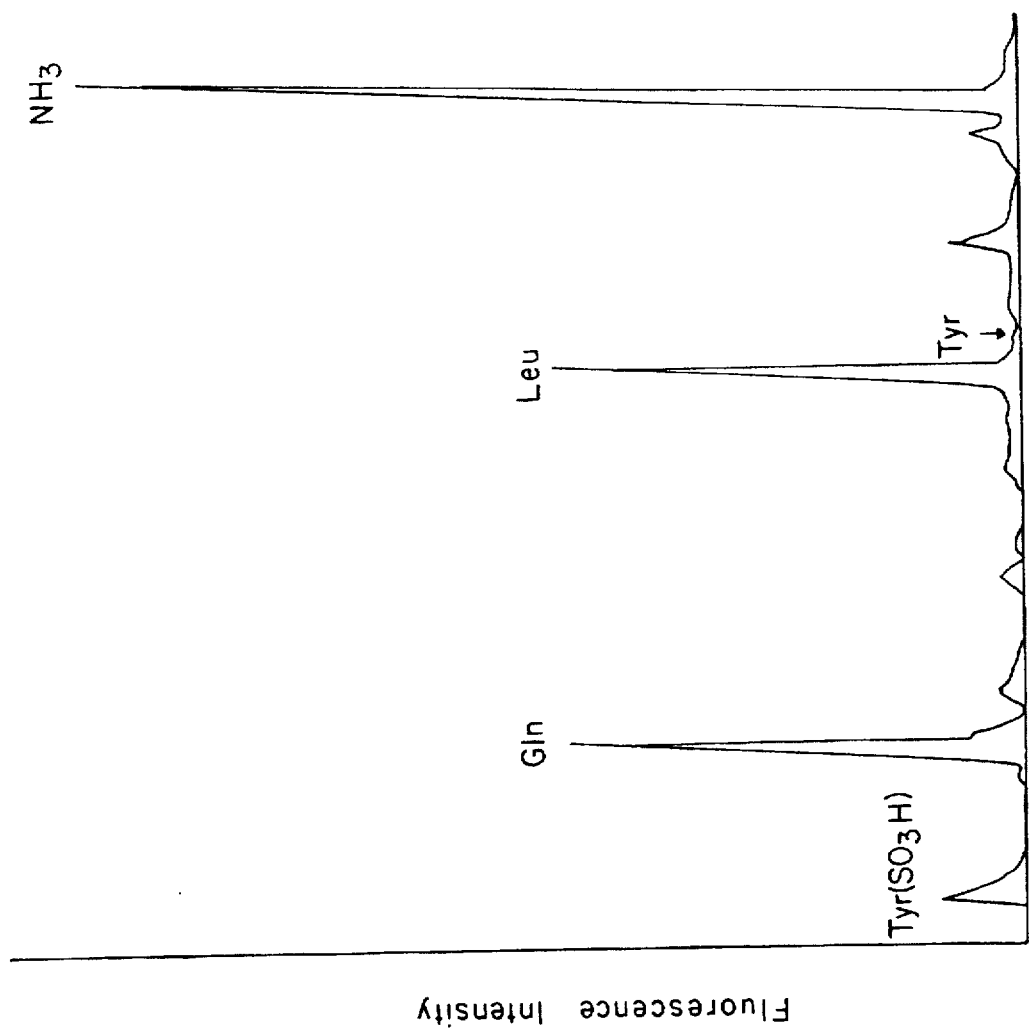
FIG. 4 shows profile of amino acid chromatogram of carboxypeptidase Y digested sulfated peptide(A) described in example 2.

(1) Identification of sulfated site of peptide (A)

a. Amino acid analysis after aminopeptidase M digestion
To 10 µl of 1 mM substrate, 5 µl (250 ng) of α-chymotrypsin (product of Sigma, TLCK treated) was added under ice cold condition, followed by 4 hours digestion in 0.1M sodium-phosphate buffer (pH7.0) at the temperature of 37° C. To this reaction mixture, 5 µl of aminopeptidase M (product of Pierce, 5 mg/ml) was added and an additional 18 hours hydrolysis was carried out. Sulfated peptide (A) was confirmed to be a mono-sulfated compound by the values of amino acid composition analysis after the hydrolysis.

b. Digestion by carboxypeptidase Y To 10 µl of 1 mM substrate, 1 mg/ml carboxypeptidase Y (product of Boehringer Mannheim) was added under ice cold condition, followed by 30 min. digestion in 0.1M sodium-phoshate buffer (pH7.0) at the temperature of 37° C. After the digestion, analysis was done using an amino acid analyzer (o-phthal aldehyde method). By the chromatogram in FIG. 4, it was confirmed that amino acids Gln, Leu, Tyr(SO₃H) were released from the C-terminal side of peptide (A), and no Tyr was released.

From the results in a. and b. above, the sulfated peptide (A) was confirmed to be a mono-sulfated compound of which the C-terminal side Tyr was sulfated.

(2) Identification of sulfated site of peptide (B)

a. Amino acid analysis after aminopeptidase M digestion

Three kinds of sulfated peptide (B) (peaks 1-3 in FIG. 3) were hydrolysed by using aminopeptidase M as described in (1)-a. From the values of amino acid analysis after the hydrolysis, the peak 1 was confirmed to be a disulfated compound, peaks 2 and 3 were confirmed to be monosulfated compounds.

b. Peptide mapping by chymotrypsin digestion

To 10 µl of 1 mM substrate, 5 µl (250 ng) of (α-chymotrypsin was added under ice cold conditions, followed by 24 hours digestion in 0.1M sodium-phoshate buffer (pH7.0) at the temperature of 37° C. This reaction mixture was loaded on a reverse phase HPLC having Nucleosil SCIs (4×150 mm) as stationary phase, and elution points of a digested peptides were confirmed. As the result, when the substrate was non-sulfated peptide (B), 2 fragments composed of 8 amino acids and 4 amino acids were generated by cleavage of the amide bond after the Tyr on the N-terminal side. Similarly, three kinds of sulfated compounds of peaks 1-3 were treated in the same way, and in all three cases, the elution point of fragment composed of 8 amino acids was identical to that of the non-sulfated peptide. This result shows that in all three kinds of sulfated peptides, the Tyr of the N-terminal side was not sulfated. Therefore, putting this result and the result in a. together, peak 1 was confirmed to a be disulfated compound having two sulfated Tyr residues on the C-terminal side.

c. Digestion by V8 protease

To 10 µl of 1 mM substrate, 5 µl (2.5 unit) of V8 protease (product of Sigma) was added under ice cold conditions, followed by 1 hour digestion in 0.1M sodium-phosphate buffer (pH7.0) at the temperature of 37° C. This reaction mixture was loaded on reverse phase HPLC having Nucleosil 5C₁₈ (4×150 mm) as the stationary phase, and elution points of the digested peptides were confirmed. As the result of being sulfated, two fragments composed of eight amino acids and four amino acids were generated from the peptide (A) as the substrate by cleavage of the amide bond between Glu and Tyr on the N-terminal side. Among them, the elution point of the fragment composed of 4 amino acids, that is Tyr-Tyr(SO₃H)-Leu-Gln, was found to be identical with the elution point of the fragment composed of 4 amino acids generated by digestion of the peak 3, which is one of the fragments generated by chymotrypsin digestion of peaks 1-3 in above b. From this result, peak 3 was confirmed to be a monosulfated compound having Tyr on C-terminal side sulfated. And since the peak 2 having a different elution point was shown to be a monosulfated compound like peak 3 from above a., it was identified as -Tyr-Tyr(SO₃H)-Tyr.

The above results in (1) and (2) on identification of sulfation site are summarized below.

| Sulfated Compound | Structure |
|---|---|
| Peptide (A) (SEQ. ID. NO.:2): | Gly—Asp—Phe—Glu—Glu—Ile—Pro—Glu—Tyr—Tyr(SO₃H)—Leu—Gln |
| Peptide (B) (SEQ. ID. NO.:13) | |
| Peak 1: | Gly—Asp—Phe—Glu—Glu—Ile—Pro—Tyr—Tyr(SO₃H)—Tyr(SO₃H)—Leu—Gln |
| Peak 2: | Gly—Asp—Phe—Glu—Glu—Ile—Pro—Tyr—Tyr(SO₃H)—Tyr—Leu—Gln |
| Peak 3: | Gly—Asp—Phe—Glu—Glu—Ile—Pro—Tyr—Tyr—Tyr(SO₃H)—Leu—Gln |

Example 3

Production of (C) Suc-Gly-Asp-Phe-Glu-Pro-Ile-Pro-Glu-Tyr-Tyr-Leu-Gln—OH, SEQ. ID. NO:4

(D) Suc-Gly-Asp-Phe-Glu-Pro-Ile-Pro-Glu-Tyr-Tyr-Leu-Gln—NH₂, SEQ. ID. NO:4

(E) Suc-Gly-Asp-Phe-Glu-Pro-Ile-Pro-Tyr-Tyr-Tyr-Leu-Gln—OH, SEQ. ID. NO:5

(F) Suc-Asp-Phe-Glu-Pro-Ile-Pro-Glu-Tyr-Tyr-Leu-Gln—OH, SEQ. ID. NO:6

(G) Suc-Phe-Giu-Pro-Ile-Pro-Glu-Tyr-Tyr-Leu-Gln—OH, SEQ. ID. NO:7 and (H) Suc-Glu-Pro-BIe-Pro-Glu-Tyr-Tyr-Leu-Gln—OH SEQ. ID. NO:8

Boc-Gln-OCH2-PAM resin (0.5 mM) was used as the starting material for abovementioned peptides (C), (E), (F), (G) and (H), and p-methyl BHA resin (0.5 mM) for (D). The synthesis was done according to the method described in Example 1, and after the peptide chain elongation, succinylization of the N-terminal was done with succinic acid anhydride to obtain protected peptides bound to resin. The peptides bound to resin were deprotected and purified according to the method described in Example 1 to yield abovementioned peptides (C), (D), (E), (F), (G) and (H). The thus obtained peptides were hydrolysed with 6N hydrochloric acid at 110° C. for 24 hours followed by amino acid analysis, and the result in the following table showed the peptides to be the aforementioned desired peptides.

| Amino Acid | (C) | (D) | (E) | (F) | (G) | (H) |
|---|---|---|---|---|---|---|
| Asx | 1.01 (1) | 0.97 (1) | 1.01 (1) | 1.01 (1) | | |
| Glx | 3.25 (3) | 2.70 (3) | 2.13 (2) | 3.06 (3) | 3.05 (3) | 3.06 (3) |
| Gly | 1.00 (1) | 1.00 (1) | 1.00 (1) | | | |
| Ile | 1.00 (1) | 0.92 (1) | 0.95 (1) | 0.97 (1) | 0.98 (1) | 0.98 (1) |
| Leu | 1.05 (1) | 0.96 (1) | 1.01 (1) | 1.03 (1) | 1.04 (1) | 1.03 (1) |
| Tyr | 2.07 (2) | 1.86 (2) | 2.91 (3) | 1.97 (2) | 1.98 (2) | 1.97 (2) |
| Phe | 1.02 (1) | 0.95 (1) | 0.98 (1) | 1.01 (1) | 1.00 (1) | |
| Pro | 1.71 (2) | 1.75 (2) | 1.93 (2) | 1.96 (2) | 1.95 (2) | 1.95 (2) |

Figures in parenthesis show the theoretical value

Example 4

Production of sulfated form of (C) Suc-Gly-Asp-Phe-Glu-Pro-Ile-Pro-Glu-Tyr-Tyr-Leu-Gln—OH, SEQ. ID. NO:4

(D) Suc-Gly-Asp-Phe-Gln-Pro-Ile-Pro-Glu-Tyr-Tyr-Leu—NH₂, SEQ. ID. NO:4

(E) Suc-Gly-Asp-Phe-Glu-Pro-Ile-Pro-Tyr-Tyr-Leu-Gln—OH, SEQ. ID. NO:5

(F) Suc-Asp-Phe-Glu-Pro-Ile-Pro-Glu-yr-Tyr-Leu-Gln—OH, SEQ. ID. NO:6

(G) Suc-Phe-Glu-Pro-Ile-Pro-Glu-Tyr-T r-Leu-Gln—OH, SEQ. ID. NO:7 and (H) Suc-Glu-Pro-Ile-Pro-Glu-Tyr-Tyr-Leu-Gln—OH SEQ. ID. NO:8

Each of 50 mg of peptides (C), (D), (F), (G) and (14) produced in Example 3 were dissolved in 4 ml of 20% pyridine/dimethyl-formamide, followed by sulfation by addition of 1.05 g (225 equivalent) of pyridine-sulfur trioxide at room temperature (25° C.), and 4 hours of reaction time.

On the other hand, peptide (E) was sulfated by condensation using diceclohexylcarbodiimide(DCC). That is, to 1 µmol of this peptide, 10 µl of dimethylformamide containing 40 µimol of concentrated sulfuric acid was added, and sulfation was carried out at room temperature(25° C.) for 1 minute with stirring.

Sulfated compounds obtained by the aforementioned process were purified using reverse phase HPLC under the following conditions.

| Equipment: | Shimazu LC-6A |
|---|---|
| Column: | Waters µ-Bondapak $C_{18}$ (3.9 × 300 mm) |
| Running Buffer: | 0.1% trifluoroacetate, acetonitrile |
| Gradient: | acetonitrile 10–60%/50 min. |
| Flow rate: | 1.5 ml/min. |
| Detection: | 230 nm |

Under these conditions, sulfated peptide (D) eluted at 18.7 minutes, sulfated (E) at 17.6 minutes, sulfated (F) at 18.0 minutes, sulfated (G) at 19.3 minutes and sulfated (H) at 13.6 minutes, respectively. Each sulfated compound was collected, concentrated, desalted by gel filtration (product of Pharmacia, Sephadex G-10), pH adjusted at 7.0–7.5 with 10% aqueous ammonia and lyophilized. By this method, stable sulfated compounds were recovered as ammonium salts.

Identification of sulfation site

According to the method of the identification of sulfated site described in Example 2, sulfated sites of the abovementioned sulfated peptides were identified. As a result, the structure of each sulfated compound became clear as shown below.

| Sulfated compound | Structure |
|---|---|
| Peptide (C) (SEQ. ID. NO.:4): | Suc—Gly—Asp—Phe—Glu—Pro—Ile—Pro—Glu—Tyr($SO_3H$)—Tyr($SO_3H$)—Leu—Gln—OH |
| Peptide (D) (SEQ. ID. NO.:4): | Suc—Gly—Asp—Phe—Glu—Pro—Ile—Pro—Glu—Tyr($SO_3H$)—Tyr($SO_3H$)—Leu—Gln—$NH_2$ |
| Peptide (E) (SEQ. ID. NO.:5): | Suc—Gly—Asp—Phe—Glu—Pro—Ile—Pro—Tyr($SO_3H$)—Tyr($SO_3H$)—Tyr($SO_3H$)—Leu—Gln—OH |
| Peptide (F) (SEQ. ID. NO.:6): | Suc—Asp—Phe—Glu—Pro—Ile—Pro—Glu—Tyr($SO_3H$)—Tyr($SO_3H$)—Leu—Gln—OH |
| Peptide (G) (SEQ. ID. NO.:7): | Suc—Phe—Glu—Pro—Ile—Pro—Glu—Tyr($SO_3H$)—Tyr($SO_3H$)—Leu—Gln—OH |
| Peptide (H) (SEQ. ID. NO.:8): | Suc—Glu—Pro—Ile—Pro—Glu—Tyr($SO_3H$)—Tyr($SO_3H$)—Leu—Gln—OH |

Example 5

Production of (I) Suc-Phe-Glu-Pro-Ile-Pro-Glu-Tyr-Tyr—OH, (J) Suc-Phe-Glu-Pro-Ile-Pro-Glu-Tyr-Tyr—$NH_2$, (K) Suc-Phe-Glu-Pro-Ile-Pro-Glu-Tyr-Tyr—$NH(CH_2)_2$COOH, (L) Suc-Phe-Glu-Pro-Ile-Pro-Glu-Tyr-Tyr—$NH(CH_2)_4$COOH, (M) Suc-Phe-Glu-Pro-Ile-Pro-Glu-Tyr-Tyr-Tau—$NH_2$, (N) Suc-Phe-Glu-Pro-Ile-Pro-Glu-Tyr-TYr—$NH(CH_2)_3$OH, and (O) Suc-Phe-Glu-Pro-Ile-Pro-Glu-Tyr-Tyr-(L)Asu(OMe)OMe, I—O are all encompassed by SEQ. ID. NO.:9)

As the starting material used for all abovementioned peptides (1), (J), (K), (L), (M), (N) and (O), the protected peptide shown in the following formula (i) was first produced by the liquid phase method.

(i) Boc-Phe-Glu(OBzl)-Pro-Ile-Pro-Glu(OBzl)-Tyr(Bzl—$Cl_2$)-Tyr(Bzl—$Cl_2$)-OH

Peptide (i) was obtained by the following procedures. After the Boc group was removed from the starting material Boc-Tyr(Bzl—$Cl_2$)OPac (OPac stands for phenacyl ester) with trifluoroacetate, condensation was done with Boc-Tyr (Bzl—ClI)—OH by the DCC-HOBt method and Boc-Tyr (Bzl—$Cl_2$)-Tyr(Bzl—$Cl_2$)-OPac was obtained. Then, starting from Boc-Tyr(Bzl—$C_{12}$)-Tyr(Bzl—$Cl_2$)-OPac, according to the aforementioned method, elongation of the peptide was done by repeated deprotection and condensation of protected amino acids in order, and the protected peptide shown in the following formula (ii) was obtained.

(ii) Boc-Phe-Glu(OBzl)-Pro-Ile-Pro-Glu(OBzl)-Tyr(Bzl—$Cl_2$)-Tyr(Bzl—C2)-OPac

After peptide (ii) was dissolved in acetate in water dipped container, zinc powder was added to it, stirred for 2 hours, was removed the zinc powder from the reaction mixture, concentrated under vacuum pressure and abovementioned peptide (i) was obtained.

Abovementioned peptide (I) was synthesized by the following procedure using peptide (i) as starting material.

First, the Boc group was removed from peptide (i) with trifluoroacetate, followed by treating it with succinic acid anhydride in the presence of base and the protected peptide (iii) shown in the formula below was obtained.

(iii) Suc-Phe-Glu(OBzl)-Pro-Ile-Pro-Glu(OBzl)-Tyr(Bzl—$Cl_2$)-Tyr(Bzl—$Cl_2$)-OH Peptide (iii) was treated with hydrogenfluoride at 0° C. for 1 hour in the presence of anisole to remove all the protecting groups. After the removal, hydrogenfluoride was removed under vacuum pressure, the residue was washed with diethylether and dissolved in 1N acetic acid, charged on highly basic ion exchange column (Diaion PA-308), and the peptide was eluted by 50% acetic acid.

Then, purification was done by gel filtration under following conditions.

| Column: | Sephadex LH-20 (2.2 φ × 97 cm) |
| --- | --- |
| Running buffer: | 50% MeOH/H$_2$O |
| Flow rate: | 0.8 ml/min. |
| Detection: | UV 230 nm, 280 nm |

The appropriate portion was collected and lyophilized to obtain the aimed compound (I).

Abovementioned peptide (J) was synthesized by the following procedure using peptide (i) as starting material.

First, DCC-HOSu was reacted with a chloroform solution of peptide (i) to convert peptide (i) to an activated ester. To this solution, ammonium gas was introduced, followed by vacuum concentration, removal of Boc group from the obtained residue with a procedure similar to the synthesis of (I), succinylization, and protected peptide (iv) shown in the formula below was obtained.

(iv) Suc-Phe-Glu(OBzl)-Pro-Ile-Pro-Glu(OBzl)-Tyr-(Bzl—Cl$_2$)-Tyr(Bzl—Cl$_2$)-NH$_2$

Peptide (iv) was treated with hydrogenfluoride at 0° C. for 1 hour in the presence of anisole to remove all the protecting groups. After the removal, hydrogen fluoride was removed under vacuum pressure, the residue was washed with diethylether and dissolved in 1N acetic acid, charged on highly basic ion exchange column, and the peptide was eluted by 50% acetic acid. Then, purification was done by gel filtration under the following condition. The appropriate portion was collected and lyophilized to obtain the desined compound (J).

Abovementioned peptide (K) was synthesized by the following procedure using peptide (i) as starting material.

First, condensation of peptide (i) and NH$_2$(CH$_2$)$_2$COOBzl·HCl was done by the DCC-HOBt method and following protected peptide (v) was obtained.

(v) Boc-Phe-Glu(OBzl)-Pro-Ile-Pro-Glu(OBzl)-Tyr(Bzl—Cl$_2$)-Tyr(Bzl—Cl$_2$)—NH(CH$_2$)$_2$COOBzl

The Boc group of peptide (v) was removed by the method similar to the a one described in abovementioned synthesis of (I), followed by succinylization of the N-terminal end, deprotection of the obtained protected peptide by the a method similar to the one described in abovementioned synthesis of (I), purified and the desired compound (K) was obtained.

Abovementioned peptide (L) was synthesized by the following procedure using peptide (i) as starting material.

First, using peptide (i) and NH$_2$(CH$_2$)$_4$COOBzl·HCl, the following protected peptide (vi) was obtained by the method similar to abovementioned peptide (K).

(vi) Boc-Phe-Glu(OBzl)-Pro-Ile-Pro-Glu(OBzl)-Tyr(Bzl—Cl$_2$)-Tyr(Bzl—Cl$_2$)—NH(CH$_2$)$_4$COOBzl

By the method similar to abovementioned peptide (K), the N-terminal end of peptide (vi) was succinylized, followed by deprotection of the obtained protected peptide by the method similar to the one described in the abovementioned synthesis of (K), purified, and the desiredcompound (L) was obtained.

Abovementioned peptide (M) was synthesized by the following procedure using peptide (i) as starting material.

First, using peptide (i) and Tau—NH$_2$·HCl, the following protected peptide (vii) was obtained by the method similar to abovementioned peptide (K).

(vii) Boc-Phe-Glu(OBzl)-Pro-Ile-Pro-Glu(OBzl)-Tyr(Bzl—Cl$_2$)-Tyr(Bzl—Cl$_2$)-Tau-NH$_2$ By the method similar to abovementioned peptide (K), the N-terminal end of peptide (vii) was succinylized, followed by deprotection of the obtained protected peptide by the method similar to the one described in abovementioned synthesis of (K), purified, and the desired compound (M) was obtained.

Abovementioned peptide (N) was synthesized by the following procedure using peptide (i) as starting material.

First, using peptide (i) and H$_2$N(CH$_2$)$_3$OH, the following protected peptide (viii) was obtained by the method similar to abovementioned peptide (K).

(viii) Boc-Phe-Glu(OBzl)-Pro-Ile-Pro-Glu(OBzl)-Tyr(Bzl—Cl$_2$)-Tyr(Bzl—Cl$_2$)—NH(CH$_2$)$_3$OH By the method similar to abovementioned peptide (K), the N-terminal end of peptide (viii) was succinylized, followed by deprotection of the obtained protected peptide by the method similar to the one described in the abovementioned synthesis of (K), purified, and the desired compound (N) was obtained.

Abovementioned peptide (O) was synthesized by the following procedure using peptide (i) as starting material.

First, using peptide (i) and (L)Asu(OMe)OMe·HCl, the following protected peptide (ix) was obtained by the method similar to abovementioned peptide (K).

(ix) Boc-Phe-Glu(OBzl)-Pro-Ile-Pro-Glu(OBzl)-Tyr(Bzl—Cl$_2$)-Tyr(Bzl—Cl$_2$)-(L)Asu(OMe)OMe

By the method similar to abovementioned peptide (K), the N-terminal end of peptide (ix) was succinylized, followed by deprotection of the obtained protected peptide by the method similar to the one described in abovementioned synthesis of (K), purified, and the desired compound (O) was obtained.

Followings are results of amino acid analysis after hydrolysis of these peptides in 6N hydrochloride 110° C. for 24 hours, and Rf value of thin layer chromatography. The results show the abovementioned aimed peptides were obtained.

| Amino Acid | (I) | (J) | (K) | (L) | (M) | (N) | (O) |
| --- | --- | --- | --- | --- | --- | --- | --- |
| Glu | 2.17(2) | 2.13(2) | 2.12(2) | 2.14(2) | 2.15(2) | 2.19(2) | 2.15(2) |
| Pro | 2.08(2) | 1.89(2) | 2.00(2) | 1.83(2) | 1.84(2) | 1.83(2) | 2.09(2) |
| Ile | 0.98(1) | 0.96(1) | 0.91(1) | 0.95(1) | 0.99(1) | 1.00(1) | 0.93(1) |
| Tyr | 1.92(2) | 2.12(2) | 2.01(2) | 2.11(2) | 2.13(2) | 2.15(2) | 2.11(2) |
| Phe | 1.00(1) | 1.00(1) |  | 1.00(1) | 1.00(1) | 1.00(1) | 1.00(1) |
| Tau-NH$_2$ |  |  |  | 1.11(1) |  |  |  |
| Asu |  |  |  |  |  |  | 0.98 (1) |
| NH$_2$(CH$_2$)$_2$COOH + Phe |  |  | 1.93 (2) |  |  |  |  |
| NH$_2$(CH$_2$)$_4$COOH |  |  |  | 0.89 (1) |  |  |  |

| Figures in parenthesis show the theoretical value | | | | | | | |
|---|---|---|---|---|---|---|---|
| TLC | (I) | (J) | (K) | (L) | (M) | (N) | (O) |
| I | 0.63 | 0.71 | 0.71 | 0.66 | 0.68 | 0.72 | 0.84 |
| II | 0.54 | 0.59 | 0.55 | 0.52 | 0.59 | 0.59 | 0.64 |

Merck 20×20 silica gel 60 glass plates $F_{254}$, 0.25 mm thickness
I; $CHCl_3$/MeOH/AcOH (5/2/1)
II; n-BuOH/AcOH/$H_2$/Pyridine (15/3/12/10)

Example 6
Production of sulfated form of
(I) Suc-Phe-Glu-Pro-Ile-Pro-Glu-Tyr-Tyr—OH,
(J) Suc-Phe-Glu-Pro-Ile-Pro-Glu-Tyr-Tyr—$NH_2$,
(K) Suc-Phe-Glu-Pro-Ile-Pro-Glu-Tyr-Tyr—NH($CH_2$)$_2$COOH,
(L) Suc-Phe-Glu-Pro-Ile-Pro-Glu-Tyr-Tyr—NH($CH_2$)$_4$COOH,
(M) Suc-Phe-Glu-Pro-Ile-Pro-Glu-Tyr-Tyr-Tau—$NH_2$,
(N) Suc-Phe-Glu-Pro-Ile-Pro-Glu-Tyr-Tyr—NH($CH_2$)$_{30}$H, and
(O) Suc-Phe-Glu-Pro-Ile-Pro-Glu-Tyr-Tyr—(L)Asu(OMe)OMe, (peptides I—O are all encompassed by SEQ. ID. NO.:9)

Each of 50mg of peptides (I), (J), (K), (L), (M), (N) and (O), produced in Example 5, were dissolved in 20 ml of pyridine/dimethylformamide (1:1), 1.29 g (200 equivalents) of pyridine-sulfur trioxide was added at room temperature (25° C.), and 4 hours reaction was carried out for sulfation. Then the sulfated compounds were adjusted to pH7.0 with aqueous saturated solution of sodium hydrogen carbonate, precipitates were filtered and filtrates were concentrated under reduced pressure.

The aforementioned sulfated compounds were purified by reverse phase HPLC under the following conditions.

| Equipment: | Nihon Bunkou 808-SC |
|---|---|
| Column: | Waters µ-Bondapak 5$C_{18}$ (3.9 × 300 mm) |
| Running Buffer: | Methanol, 10 mM ammonium acetate aqueous solution (pH 6.0) |
| Gradient: | Methanol 1 → 60%/60 min. |
| Flow rate: | 1 ml/min. |
| Detection: | 230 nm and 280 nm |

Under these conditions, each sulfated compound was collected and lyophilized, and the obtained powder was dissolved in 0.05N acetic acid and desalted by Sephadex G-10. Appropriate portions were collected and lyophilized to obtain the aimed sulfated compounds as sodium salts.
Identification of sulfation site The sites of sulfation of the abovementioned sulfated peptides were identified according to the method of identification of sulfation site described in Example 2. As the result, structure of each sulfated compound became clear as shown below SEQ. ID. NO.:9.

| Sulfated Compound | Structure |
|---|---|
| Peptide (I) | Suc—Phe—Glu—Pro—Ile—Pro—Glu—Tyr($SO_3H$)—Tyr($SO_3H$)—OH |
| Peptide (J) | Suc—Phe—Glu—Pro—Ile—Pro —Glu—Tyr($SO_3H$)—Tyr($SO_3H$)—$NH_2$ |
| Peptide (K) | Suc—Phe—Glu—Pro—Ile—Pro—Glu—Tyr($SO_3H$)—Tyr($SO_3H$)—NH($CH_2$)$_2$COOH |
| Peptide (L) | Suc—Phe—Glu—Pro—Ile—Pro—Glu—Tyr($SO_3H$)—Tyr($SO_3H$)—NH($CH_2$)$_4$COOH |
| Peptide (M) | Suc—Phe—Glu—Pro—Ile—Pro—Glu—Tyr($SO_3H$)—Tyr($SO_3H$)—Tau—$NH_2$ |
| Peptide (N) | Suc—Phe—Glu—Pro—Ile—Pro—Glu—Tyr($SO_3H$)—Tyr($SO_3H$)—NH($CH_2$)$_3$OH |
| Peptide (O) | Suc—Phe—Glu—Pro—Ile—Pro—Glu—Tyr($SO_3H$)—Tyr($SO_3H$)—(L)Asu(OMe)OMe |

Example 7
Production of
(P) Suc-Phe-Glu-Pro-Ile-Pro-Glu-Tyr-Tyr-leu-ol,
(Q) Suc-Phe-Glu-Pro-Ile-Pro-Glu-Tyr-Tyr-Leu—OH,
(R) Suc-Phe-Glu-Pro-Ile-Pro-Glu-Tyr-Tyr-Leu—NHEt,
(S) Suc-Phe-Glu-Pro-Ile-Pro-Glu-Tyr-Tyr-Leu-Tau—$NH_2$,
(T) Suc-Phe-Glu-Pro-Ile-Pro-Glu-Tyr-Tyr-Leu-(D)Glu—OH,
(U) Suc-Phe-Glu-Pro-Ile-Pro-Glu-Tyr-Tyr-Leu-(D)Asu(OMe)OMe,
(V) Suc-Phe-Glu-Pro-Ile-Pro-Glu-Tyr-Tyr-Leu-(L)Asu(OMe)OMe,
(W) Suc-Phe-Glu-Pro-Ile-Pro-Glu-Tyr-Tyr-Leu-(D)Asu(NTH$_2$)NH$_2$,
(X) Suc-Phe-Glu-Pro-Ile-Pro-Glu-Tyr-Tyr-Leu-(L)Asu(NH$_2$)NH$_2$, and
(Y) Suc-Phe-Glu-Pro-Ile-Pro-Glu-Tyr-Tyr-Leu—NHPO(OH)$_2$ As the starting material used for all abovementioned peptides (Q), (R), (S), (T), (U), (V), (W) and (X), the protected peptide shown in the following formula (x) was first produced by liquid phase method.
(x) Boc-Phe-Glu(OBzl)-Pro-Ile-Pro-Glu(OBzl)-Tyr(Bzl—Cl$_2$)-Tyr(Bzl—Cl$_2$)-Leu—OH Peptide (x) synthesis was done as follows. First, condensation of protected peptide (i) synthesized in Example 5 and TosOH·Leu-OTce (OTce stands for 2,2,2-trichloroethylester) was done by WSCI-HOBt method and peptide (xi) shown in the formula below was synthesized.
(xi) Boc-Phe-Glu(OBzl)-Pro-Ile-Pro-Glu(OBzl)-Tyr(BZl—Cl$_2$)-Tyr(BZl—Cl$_2$)-Leu-OTce Next, after peptide (xi) was dissolved in acetate in water dipped container, zinc powder was added to it, stirred for 2 hours for Tce deprotection, the zinc powder was removed from the reaction mixture, concentrated under vacuum pressure and the abovementioned peptide (x) was obtained.

Abovementioned peptide (P) was synthesized by the following procedure using peptide (i) as starting material.

First, condensation of peptide (i) and Leu-ol was done by WSCI-HOBt method and protected peptide (xii) shown in the formula below was obtained.
(xii) Boc-Phe-Glu(OBzl)-Pro-Ile-Pro-Glu(OBzl)-Tyr(Bzl—Cl$_2$)-Tyr(Bzl—Cl$_2$)-Leu-ol The Boc group was removed from peptide (xii) according to the synthesis method of (I), the N-terminal end of peptide (xii) was succinylized, followed by deprotection of the obtained protected peptide by the method similar to the one described in abovementioned synthesis of (I), purified, and the aimed compound (P) was desired.

Above mentioned peptide (Q) was synthesized by the following procedure using peptide (x) as starting material.

First, the Boc group was removed from peptide (x) with trifluoroacetate, followed by treating it with succinic acid anhydride in the presence of base and the protected peptide (xiii) shown in the following formula was obtained.

(xiii) Suc-Phe-Glu(OBzl)-Pro-Ile-Pro-Glu(OBzl)-Tyr(Bzl—Cl$_2$)-Tyr(Bzl—Cl$_2$)-Leu-OH Peptide (xiii) was treated with anhydrous hydrogen fluoride at 0° C. for 1 hour in the presence of anisole to remove all the protecting groups. After the removal, hydrogen fluoride was removed under vacuum pressure, residue was washed with diethylether and dissolved in 1N acetic acid, charged on a highly basic ion exchange column, and peptide was eluted by 50% acetic acid. Then, purification was done by gel filtration under the condition described before and desired compound (Q) was obtained.

Abovementioned peptide (R) was synthesized by the following procedure using peptide (x) as starting material.

First, condensation of peptide (x) and Nl-I2Et was done by WSCI-HOBt method and protected peptide (xiv) shown in the formula below was obtained.

(xiv) Boc-Phc-Glu(OBzl)-Pro-Ile-Pro-Glu(OBzl)-Tyr(Bzl—Cl$_2$)-Tyr(Bzl—Cl$_2$)-Leu-NH$_2$Et The Boc group was removed from peptide (xiv) according to the synthesis method of (Q), followed by succinylization of the N-terminal, deprotection of obtained protected peptide according to the synthesis method of (Q), purified, and desired compound (R) was obtained.

Abovementioned peptide (S) was synthesized by the following procedure using peptide (x) as starting material.

First, protected peptide (xv) shown in the formula below was obtained using peptide (x) and Tau—NH$_2$·HCl by a method similar to the peptide (M).

(xv) Boc-Phe-Glu(OBzl)-Pro-Ile-Pro-Glu(OBzl)-Tyr(Bzl—Cl$_2$)-Tyr(Bzl-Cl$_2$)-Leu-Tau-NH$_2$

Succinylization of the N-terminal of peptide (xv) was done with the method similar to peptide (M), deprotection of the obtained protected peptide according to synthesis method of (M), and after the purification, desired compound (S) was obtained.

Abovementioned peptide (T) was synthesized by the following procedure using peptide (x) as starting material.

First, protected peptide (xvi) shown inthe formula below was obtained using peptide (x) and (D)Glu(OBzl)OBzl·HCl by a method similar to the peptide (S).

(xvi) Boc-Phe-Glu(OBzl)-Pro-Ile-Pro-Glu(OBzl)-Tyr(Bzl—Cl$_2$)-Tyr(Bzl-Cl$_2$)-Leu-(D)Glu(OBzl)OBzl Succinylization of the N-terminal of peptide (xvi) was done by a method similar to peptide (S), deprotection of the obtained protected peptide according to the synthesis method of (S), and after purification, desired compound (T) was obtained.

Abovementioned peptide (U) was synthesized by the following procedure using peptide (x) as starting material.

First, protected peptide (xvii) shown in the formula below was obtained using peptide (x) and (D)Asu(OMe)OMe·HCl with method similar to the peptide (S).

(xvii) Boc-Phe-Glu(OBzl)-Pro-Ile-Pro-Glu(OBzl)-Tyr(Bzl—Cl$_2$)-Tyr(Bzl—Cl$_2$)-Leu-(D)Asu(OMe)OMe Succinylization of the N-terninal of peptide (xvii) was done by a method similar to peptide (S), deprotection of the obtained protected peptide according to the synthesis method of (S), and after purification, desired compound (U) was obtained.

Abovementioned peptide (V) was synthesized by the following procedure using peptide (x) as starting material.

First, protected peptide (xviii) shown in the formula below was obtained using peptide (x) and (L)Asu(OMe)OMe·HCl with method similar to the peptide (S).

(xviii) Boc-Phc-Glu(OBzl)-Pro-Ile-Pro-Glu(OBzl)-Tyr(Bzl—Cl$_2$)-Tyr(Bzl—Cl$_2$)-Leu-(L)Asu(OMe)OMe Succinylization of the N-terminal of peptide (xviii) was done by a method similar to peptide (S), deprotection of the obtained protected peptide according to the synthesis method of (S), and after purification, desired compound (V) was obtained.

Abovementioned peptide (W) was synthesized by the following procedure using peptide (x) as starting material.

First, protected peptide (xix) shown in the formula below was obtained using peptide (x) and (D)Asu(NH$_2$)NH$_2$·HCl by a method similar to the peptide (S).

(xix) Boc-Phe-Glu(OBzl)-Pro-Ile-Pro-Glu(OBzl)-Tyr(Bzl—Cl$_2$)-Tyr(Bzl—Cl$_2$)-Leu-(D)Asu(NH$_2$)NH$_2$ Succinylization of the N-terminal of peptide (xix) was done by a method similar to peptide (S), deprotection of the obtained protected peptide according to the synthesis method of (S), and after purification, desired compound (W) was obtained.

Abovementioned peptide (X) was synthesized by the following procedure using peptide (x) as starting material.

First, protected peptide (xx) shown in the formula below was obtained using peptide (x) and (L)Asu(NH$_2$)NH$_2$·HCl by a method similar to the peptide (S).

(xx) Boc-Phe-Glu(OBzl)-Pro-Ile-Pro-Glu(OBzl)-Tyr(Bzl—Cl$_2$)-Tyr(Bzl— Cl$_2$)-Leu-(L)Asu(NH$_2$)NH$_2$

Succinylization of the N-teminal of peptide (xx) was done by a method similar to peptide (S), deprotection of the obtained protected peptide according to the synthesis method of (S), and after purification, desired compound (X) was obtained.

Abovementioned peptide (Y) was synthesized by the following procedure using peptide (i) as starting material. First, protected peptide (xxi) shown in the formula below was obtained using peptide (i) and Leu-NHPO(OH)$_2$·HCl by a method similar to the peptide (S).

(xxi) Boc-Phe-Glu(OBzl)-Pro-Ile-Pro-Glu(OBzl)-Tyr(Bzl—Cl$_2$)-Tyr(Bzl—Cl$_2$)-Leu-NHPO(OH)$_2$ Succinylization of the N-terminal of peptide (xxi) was done by a method similar to peptide (S), deprotection of the obtained protected peptide according to the synthesis method of (S), and after purification, desired compound (Y) was obtained.

Following are results of amino acid analysis after hydrolysis of these peptides in 6N hydrochloric acid at 110° C. for 24 hours, and Rf value on thin layer chromatography. The results show the abovementioned desired peptides were obtained.

| Amino Acid | (P) | (Q) | (R) | (S) | (T) |
| --- | --- | --- | --- | --- | --- |
| Glx | 2.45 (2) | 2.12 (2) | 2.21 (2) | 2.13 (2) | 3.16 (3) |
| Pro | 2.02 (2) | 2.11 (2) | 1.89 (2) | 2.08 (2) | 2.13 (2) |
| Ile | 0.95 (1) | 0.94 (1) | 0.96 (1) | 0.97 (1) | 0.94 (1) |
| Leu | — | 1.03 (1) | 1.03 (1) | 1.03 (1) | 1.02 (1) |
| Tyr | 2.12 (2) | 2.06 (2) | 2.11 (2) | 2.05 (2) | 2.10 (2) |
| Phe | 1.00 (1) | 1.00 (1) | 1.00 (1) | 1.00 (1) | 1.00 (1) |
| Tau-NH$_2$ | | | | 1.08 (1) | |

-continued

Figures in parenthesis show the theoretical value.

| Amino Acid | (U) | (V) | (W) | (X) | (Y) |
|---|---|---|---|---|---|
| Glx | 2.23 (2) | 2.18 (2) | 2.25 (2) | 2.13 (2) | 2.08 (2) |
| Pro | 1.81 (2) | 2.18 (2) | 1.83 (2) | 2.12 (2) | 1.83 (2) |
| Ile | 0.93 (1) | 0.98 (1) | 0.97 (1) | 0.94 (1) | 0.94 (1) |
| Leu | 0.92 (1) | 0.95 (1) | 1.02 (1) | 1.03 (1) | — |
| Tyr | 2.13 (2) | 2.09 (2) | 2.13 (2) | 2.01 (2) | 2.19 (2) |
| Phe | 1.00 (1) | 1.00 (1) | 1.00 (1) | 1.00 (1) | 1.00 (1) |
| Asu | 1.06 (1) | 1.10 (1) | 1.12 (1) | 1.09 (1) | |

Figures in parenthesis show the theoretical value.

| TLC | (P) | (Q) | (R) | (S) | (T) |
|---|---|---|---|---|---|
| I | 0.77 | 0.71 | 0.89 | 0.74 | 0.56 |
| II | 0.60 | 0.57 | 0.62 | 0.62 | 0.48 |

| TLC | (U) | (V) | (W) | (X) | (Y) |
|---|---|---|---|---|---|
| I | 0.93 | 0.85 | 0.75 | 0.71 | |
| II | 0.63 | 0.62 | 0.58 | 0.60 | |

Merck 20×20 silica gel 60 glass plates $F_{254}$, 0.25 mm thickness
I; $CHC_3/MeOH/AcOH$ $(5/2/1)$. II; $n$-BuOH/AcOH/$H_2O$ Pyridine (15/3/12/10)

Example 8

Production of sulfated form of
(P) Suc-Phe-Glu-Pro-Ile-Pro-Glu-Tyr-Tyr-Leu-ol,
(Q) Suc-Phe-Glu-Pro-Ile-Pro-Glu-Tyr-Tyr-Leu—OH,
(R) Suc-Phe-Glu-Pro-Ile-Pro-Glu-Tyr-Tyr-Leu-NHEt,
(S) Suc-Phe-Glu-Pro-Ile-Pro-Glu-Tyr-Tyr-Leu-Tau—$NH_2$,
(T) Suc-Phe-Glu-Pro-Ile-Pro-Glu-Tyr-Tyr-Leu-(D)Glu—OH,
(U) Suc-Phe-Glu-Pro-Ile-Pro-Glu-Tyr-Tvr-Leu-(D)Asu(OMe)OMe,
(V) Suc-Phe-Glu-Pro-Ile-Pro-Glu-Tyr-Tyr-Leu-(L)Astu(OMe)OMe,
(W) Suc-Phe-Glu-Pro-Ile-Pro-Glu-Tyr-Tyr-Leu-(D)Asu($NH_2$)$NH_2$,
(X) Suc-Phe-Glu-Pro-Ile-Pro-Glu-Tyr-Tyr-leu-(L)Asu($NH_2$)$NH_2$, and
(Y) Suc-Phe-Glu-Pro-Ile-Pro-Glu-Tyr-TYr-leu—NHPO(OH)$_2$ (peptides P—Y are all encompassed by SEQ. ID. NO.:10)

About 50 mg each of peptides (P), (Q), (R), (S), (T), (U), (V), (W), (X) and (Y), produced in Example 7, were dissolved in 20 ml of pyridine/dimethylformamide (1:1). 1.29 g (200 equivalents) of pyridine-sulfur trioxide was added at room temperature (25° C.), and 4 hours reaction was carried out for sulfation. Then, the pH was adjusted to 7.0 with saturated sodium hydrogencarbonate solution, followed by removal of precipitates deposited by this process by filtration, and condensation of filtrates under vacuum pressure.

The aforementioned sulfated compounds were purified by reverse phase HPLC under the following conditions.

| Equipment: | Nihon Bunkou 808-SC |
|---|---|
| Column: | Waters µ-Bondapak 5$C_{10}$ (3.9 × 300 mm) |
| Running Buffer: | Methanol, 10 mM ammonium acetate aqueous solution (pH 6.0) |
| Gradient: | Methanol 1 → 60%/60 min. |
| Flow rate: | 1 ml/min. |
| Detection: | 230 nm and 280 nm |

Under these conditions, each sulfated compound was collected and lyophilized, and the powder was dissolved in 0.05N acetic acid and desalted by Sephadex G-10 (product of Pharmacia). Appropriate portions were collected and lyophilized to obtain the desired sulfated compounds as sodium salts.

Identification of sulfation site

The sites of sulfation of the above-mentioned sulfated peptides were identified according to the method of identification of sulfation site described in Example 2. As the result, the structure of each sulfated compound became clear as shown below SEQ. ID. NO.:10.

| Sulfated Compound | Structure |
|---|---|
| Peptide (P) | Suc—Phe—Glu—Pro—Ile—Pro—Glu—Tyr($SO_3H$)—Tyr($SO_3H$)—Leu-ol |
| Peptide (Q) | Suc—Phe—Glu—Pro—Ile—Pro—Glu—Tyr($SO_3H$)—Tyr($SO_3H$)—Leu—OH |
| Peptide (R) | Suc—Phe—Glu—Pro—Ile—Pro—Glu—Tyr($SO_3H$)—Tyr($SO_3H$)—Leu—NHEt |
| Peptide (S) | Suc—Phe—Glu—Pro—Ile—Pro—Glu—Tyr($SO_3H$)—Tyr($SO_3H$)—Leu—Tau—$NH_2$ |
| Peptide (T) | Suc—Phe—Glu—Pro—Ile—Pro—Glu—Tyr($SO_3H$)—Tyr($SO_3H$)—Leu—(D)Glu—OH |
| Peptide (U) | Suc—Phe—Glu—Pro—Ile—Pro—Glu—Tyr($SO_3H$)—Tyr($SO_3H$)—Leu—(D)Asu(OMe)OMe |
| Peptide (V) | Suc—Phe—Glu—Pro—Ile—Pro—Glu—Tyr($SO_3H$)—Tyr($SO_3H$)—Leu—(L)Asu(OMe)OMe |
| Peptide (W) | Suc—Phe—Glu—Pro—Ile—Pro—Glu—Tyr($SO_3H$)—Tyr($SO_3H$)—Leu—(D)Asu($NH_2$)$NH_2$ |
| Peptide (X) | Suc—Phe—Glu—Pro—Ile—Pro—Glu—Tyr($SO_3H$)—Tyr($SO_3H$)—Leu—(L)Asu($NH_2$)$NH_2$ |
| Peptide (Y) | Suc—Phe—Glu—Pro—Ile—Pro—Glu—Tyr($SO_3H$)—Tyr($SO_3H$)—Leu—NHPO(OH)$_2$ |

Example 9

(1) Method of mutating Glu 61–62 of hirudin HV-1 to Tyr 61–62

The mutation primer having DNA sequence shown in formula (III) below was synthesized by the phosphoamidite method using a DNA synthesizer (Applied Biosystems 380B).

GAA ATC CCG TAC TAC TAC CTG CAG            (III)

SEQ. ID. NO.:10

1 µg of commercially available double stranded phage M13 mp19 DNA (product of Toyobo) was digested with restriction enzymes EcoRI (10 units) and HindIII (10 units) arid purified by agarose gel electrophoresis.

On the other hand, 10 µg of vector pUCHV1 (reference: Japanese Laid-Open Patent 3-164184), in which the HV-1 gene was cloned into commercially available plasmid pUC18, was digested with restriction enzymes EcoRI (30 units) and HindIII (30 units) to obtain a 210 bp DNA fragmented coding HV-1.

100 ng of this fragment and 100 ng of the above-mentioned purified EcoRI-HindIII fragment of phage M13 mp19 were ligated at 16° C. overnight using T4 DNA ligase. Using this reaction mixture, E. coli JM101 was transformed according to the method of J. Messing [Methods in Enzymology, 101, 21–78 (1983)]. From each obtained plaque, single stranded DNA (M13HV1) was prepared according to the method of J. Messing (the same as above). These were dissolved in TE buffer (pH8.0) at the final concentration of 1 mg/ml.

50 pmol of mutation primer shown in abovementioned formula (III) was phosphorylated in kinase buffer (0.1M Tris-hydrochloric acid buffer pH8.0, 0.1 mM $MgCl_2$, 7 mM Dithiothreitol, 1 mM ATP) containing 2 units of T4 polynucleotidekinase at 37° C. for 15 min, followed by heating at 70° C. for 10 min to terminate the reaction.

Mutated DNA M13HV17 was constructed using 5 µg of aforesaid M13HV1 and 4 pmol of abovementioned phosphorylated mutation oligodeoxyribonucleotide, according to the method of "Oligonucleotide-directed in vitro mutagenesis system" kit, the product of Amersham, which is an applied method of Eckstein et al. [Nucleic Acids Research, 13, 8764 (1985)]

(2) Preparation of mutated gene and construction of mutated peptide secreting plasmid 20 µl of solution containing mutated DNA M13HV17 obtained in abovementioned (1), competent *E. coli* cell TG1 was transformed and plaques were obtained. Double strand DNA was prepared from these transformants.

30 µg of abovementioned double strand DNA was digested with restriction enzymes AccI and HindIII, and a 200 bp DNA fragment having an the N-terminal amino acid coding region deleted was purified.

On the other hand, hirudin expression vector pMTSHV1 (Reference: Japanese Laid-Open Patent 2-303096) was digested with restriction enzymes AccI and HindIII as described above, and 2.75 Kb DNA fragment including DNA coding the phoA signal peptide was purified.

Figure 5:
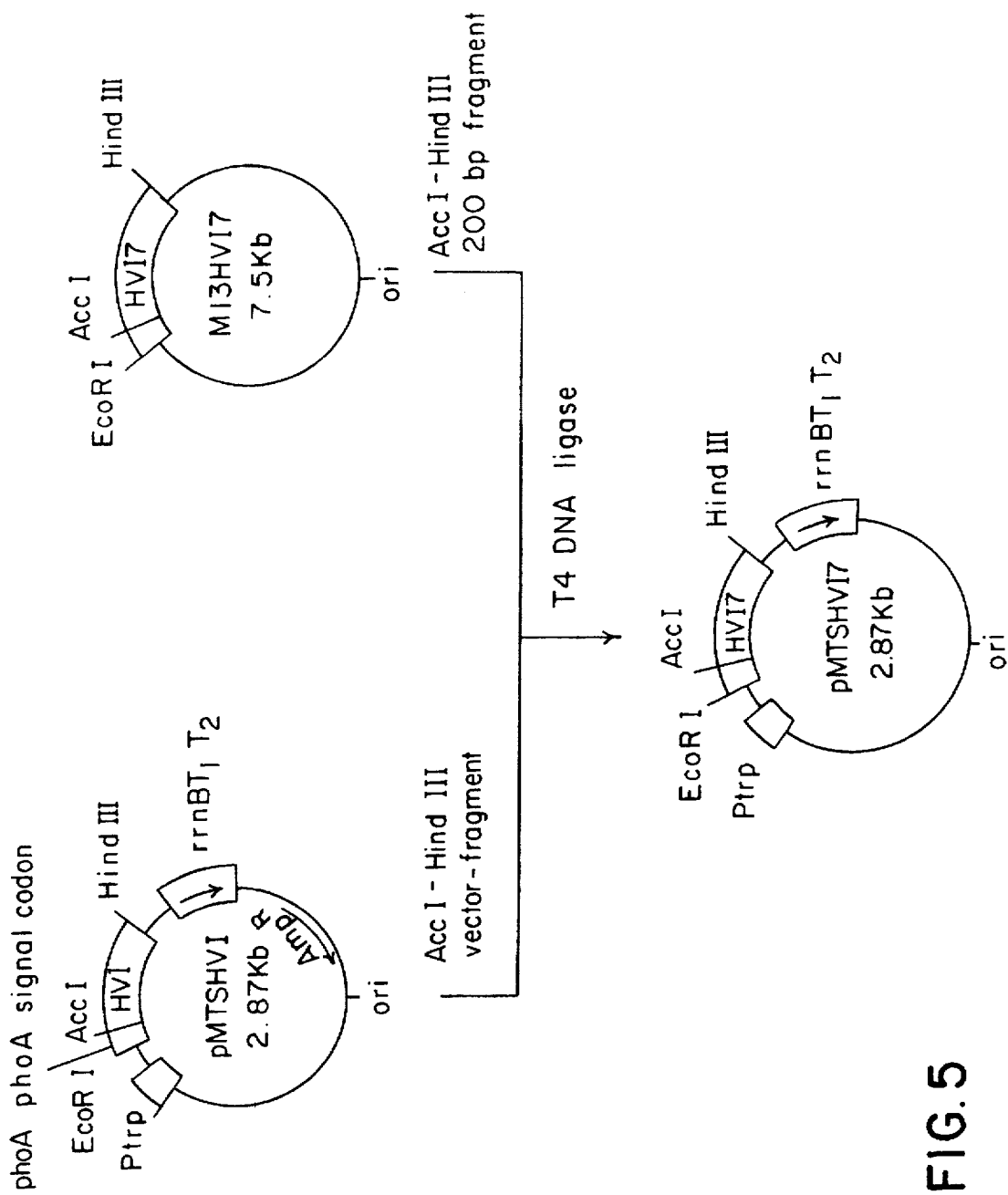
FIG. 5 shows the construction of the expression vector for hirudin HV-17 described in example 3.

Above mentioned mutated 200 bp DNA fragment and abovementioned fragment of expression vector pMTSHV1 were ligated with T4 DNA ligase (FIG. 5), with which *E. coli* JM 109 strain was transformed, and mutant expression plasmid pMTSHY17 was obtained. The DNA sequence of this plasmid was confirmed by the method of Sanger et al. Furthermore, *E. coli* RR1 was transformed using this plasmid, and higher expression than that JM 109 strain was observed.

(3) Secretion production of hirudin HV-17 by hirudin mutant HV-17 secreting plasmid *E. coli* RR1 transformed with plasmid pMTSHV17 [FERM BP-3268, deposited in the Fermentation Research Institute as *E. coli* RR1/pMTSHV17], purified in abovementioned (2), was cultured in 2 xTY medium (16 g/l bactotryptone, 10 g/l bacto-yeast extract and 5 g/l NaCl, pH 7.2) containing 100 µg/ml of ampicillin. After culturing at 37° C. for 24 hours, 1 ml of culture medium was collected. Precipitated cells were suspended in 1ml of 30mM Tris-HCl (pH7.4) containing 25% sucrose and 1 mM EDTA, followed by treating at room temperature for 10 minutes. After collecting cells by centrifugation, cells were suspended in 1 ml of cold water to release the substance in the periplasm space of the cell by osmotic shock.

Then, cells were removed by centrifugation and the supernatant was prepared. The amount of accumulated secreted mutant hirudin was determined by measuring its anti-thrombin activity in the supernatant.

The anti-thrombin activity was measured by quantitative colorimetry of the degree of inhibition of thrombin's hydrolytic activity on synthetic chromogenic substrate Chromozym TH (Tosylglycil-prolylarginine-4-nitroanilide-acetate, Boehringer-Mannheim).

This reaction was carried out as follows. To the measurement buffer (100 mM Tris—HCl (pH8.5), 150 mM NaCl and 0.1% polyethyleneglycol-6000), 0.5 units of human-thrombin.(product of Sigma) was added, the hirudin mutant was added, and pre-incubated at 37° C. for 3 minutes. To this substrate, 100 µl of ChromozymTH (product of Boehringer-Mannheim) was added to measure ΔOD405 nm/min.

A graph was drawn with amount of added hirudin mutant on the horizontal axis and ΔOD405 nm/min on the vertical axis, and the amount of hirudin causing 100% inhibition of thrombin activity was determined out from the graph, which value was defined as 0.5 anti-thrombin unit (ATU).

As a result, strain utilizing plasmid pMTSHV17 exhibited 1,310,000 ATU of anti-thrombin activity per 1 L of the culture medium, which means about 131 mg of HV-17 secretion production to the periplasmic space was observed.

(4) Secretion of HV17 into fermentor and culture medium with transformed strain of *E. coli* RR1/pMTSHV17

By a similar method described in abovementioned (3), *E. coli* RR1 strain transformed with plasmid pMTSHV17 was incubated in 2 L of 2xTY medium containing 100 µg/ml ampicillin and 2% glucose in a 5 L fermentor at 37° C. for 24 hours with aeration and agitation, and about 556 mg of HV-17 secretion production per litter of culture medium was observed.

(5) Purification of hirudin mutant HV17 from culture medium

After fermentation, 1.6 L of culture medium was collected and centrifuged to separate out cells. After the supernatant was filtered through a 3.2 µm filter (product of Pole) to remove cells completely. Hirudin mutant HV-17 was purified by chromatography in the following order.

a) Anion exchange chromatography

| Column: | QAE-toyopearl column (4.4 × 7 cm) |
|---|---|
| Running buffer: | 10 mM potassium phosphate buffer (pH7.0) |
| Elution buffer: | 0.2 M NaCl, 10 mM potassium phosphate buffer (pH7.0) | b) Gel filtration chromatography

| Column: | Sephacryl S-100 HR (4.4 × 97 cm) |
|---|---|
| Running buffer: | 10 mM potassium phosphate buffer (pH7.0) | c) Anion exchange chromatography

| Column: | DEAE-toyopearl column (4.4 × 40 cm) |
|---|---|
| Running buffer: | A. 10 mM potassium phosphate buffer (pH7.0) |
| | B. 10 mM potassium phosphate buffer (pH7.0), 0.3 M NaCl |
| Gradient: | B. 0–100%/12.5 hours | d) Reverse phase high performance liquid chromatography

| Equipment: | Waters Delta prep 3000 |
|---|---|
| Column: | Vydac C4 (4.7 × 30 cm) |
| Running buffer: | A. 0.05% trifluoroacetate/water |
| | B. acetonitrile |
| Gradient: | B. 10–60%/50 min. |
| Flow rate: | B. 80 ml/min. |

5 nmol of purified HV-17 was hydrolysed with 6N HCl at 110° C. for 24 hours and analyzed by amino acid analyzer (Beckman 7300). The result is shown in Table 1. Compared with HV-1, $HV_{17}$ was confirmed to have two less glutamic acids and two more tyrosines, which was the intention of the mutation.

Anti-thrombin activity was measured according to abovementioned (3); specific activity was 12,000 ATU/mg.

TABLE 1

| Amino Acid | Analyzed value | Theoretical value |
|---|---|---|
| Asx | 8.86 | 9 |
| Thr | 3.86 | 4 |
| Ser | 3.64 | 4 |
| Glx | 11.63 | 11 |
| Gly | 8.82 | 9 |
| Ala | — | |
| Cys | 5.63 | 6 |
| Val | 3.33 | 4 |

21

TABLE 1-continued

| Amino Acid | Analyzed value | Theoretical value |
|---|---|---|
| Met | — | |
| Ile | 1.95 | 2 |
| Leu | 4.11 | 4 |
| Tyr | 4.04 | 4 |
| Phe | 1.00 | 1 |
| His | 1.11 | 1 |
| Lys | 2.73 | 3 |
| Arg | — | |
| Pro | 3.28 | 3 |

Example 10
Production of sulfated form of hirudin mutant HV-17

Hirudin mutant HV-17, prepared in Example 9 by substituting Glu at the 61st and 62nd position with Tyr, was sulfated enzymatically using aryl sulfotransferase under the following different conditions.

| | |
|---|---|
| Hirudin mutant HV-17: | 0.1 mM |
| p-nitrophenylsulfate: | 1.0 mM |
| Sulfotransferase: | 10 U/ml |
| Magnesium chloride: | 25 mM |
| Reaction buffer: | 0.1M Tris-hydrochloric acid buffer (pH 8.6) |
| Reaction temperature: | 37° C. |
| Reaction time: | 24 hours |

Separation and collection of the sulfated form was done by HPLC under the following conditions.

| | |
|---|---|
| Column: | Nucleosil 5C$_{18}$ (4 × 150 mm) |
| Running buffer: | A. 0.1% trifluoroacetate/water |
| | B. acetonitrile |
| Gradient: | B. 1–60%/60 min. |
| Flow rate: | 1.0 ml/min. |
| Detection: | 230 nm |

Figure 6A:
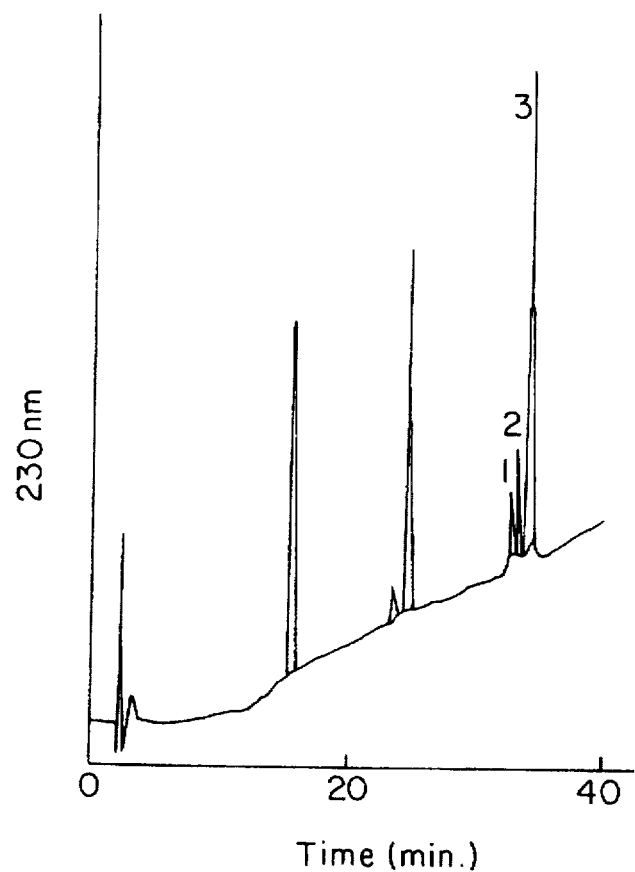
FIGS. 6A-6B shows profile of HPLC analysis chromatogram of sulfated hirudin HV-17 described in example 3.
Figure 6B:
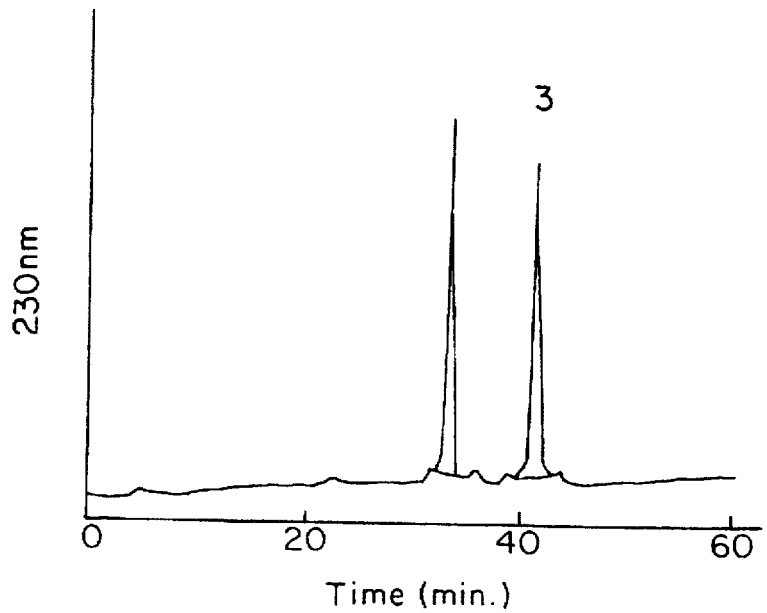

Under these conditions, sulfated forms of hirudin mutant HV-17 eluted at 32.4 minutes, 33.0 minutes, 33.7 minutes, respectively, as shown in FIG. 6 (A).

Then, after acetonitrile was removed during the process of concentration, each fraction of sulfated compound was lyophilized.

In case of peak 3, because of its insufficient separation from non-sulfated compound, further separation and collection was done by HPLC under the following conditions.

| | |
|---|---|
| Column: | TSKgel DEAE-5PW (7.5 × 75 mm) |
| Running buffer: | A. 20 mM Tris-hydrochloride buffer (pH 8.0) |
| | B. 20 mM Tris-hydrochloride buffer (pH 8.0) + 0.5M NaCl |
| Gradient: | B. 0–100%/50 min. |
| Flow rate: | 0.8 ml/min. |
| Detection: | 230 nm |

Under these conditions, sulfated forms of hirudin mutant HV-17 eluted at 40.6 minutes as shown in FIG. 6 (B). Then, each fraction of the sulfated compound was concentrated and desalted by reverse phase HPLC, followed by lyophilization.

5 Identification of sulfated site

The identification of the sulfated sites of the three kinds of separated and collected sulfated hirudin mutant HV-17 were done by using aminopeptidase M and chymotrypsin.

a) Amino acid analysis after aminopeptidase M digestion

To 10 μl of 1 mM substrate, 5 μl (250 ng) of α-chymotrypsin (product of Sigma, TLCK treated) was added under ice cold conditions, followed by 4 hours digestion in 0.1 M sodium-phosphate buffer (pH7.0) at the temperature of 37° C. To this reaction mixture, 5 ↑1 of aminopeptidase (product of Pierce, 5 mg/ml) was added and an additional 18 hours hydrolysis was carried out. Amino acid composition analysis values after the hydrolysis showed peak 1 to be a di-sulfated compound, peak 2 and peak 3 to be mono-sulfated compounds.

b) Peptide mapping by chymotrypsin digestion

To 10 ↑1 of 1 mM substrate, 5 ↑1 (250 ng) of α-chymotrypsin was added under ice cold conditions, followed by 24 hours digestion in 0.1 M sodium-phosphate buffer (pH7.0) at the temperature of 37° C. This reaction mixture was loaded on a reverse phase HPLC having Nucleosil 5C$_{18}$ (4 ×150 mm) as the stationary phase, and elution points of the digested peptides were confirmed. As the result, when the substrate was non-sulfated hirudin mutant HV-17, two fragments composed of 61 amino acids and four amino acids were generated, by cleavage of the amide bond after the 61st Tyr. Similarly, when three kinds of sulfated compounds of peaks 1—3 were treated in the same way, in all three cases, the elution points of fragment composed of 61 amino acids were identical to that of the non-sulfated peptide. This result shows that in all three kinds of sulfated peptides, the 3rd and 61st Tyr were not sulfated. Therefore, putting this result and the result in a) together, peak 1 was confirmed to be a disulfated compound having the two Tyr residues at the 62nd and 63rd positions sulfated. Also, the elution point of the fragment composed of four amino acids, obtained by digestion of peak 2 and peak 3, was identical with the elution point of the fragment composed of four amino acids generated by chymotryptic digestion of peak 2 and peak 3 in the case of peptide (B), which fragment is among the fragments generated by chymotrypsin digestion of peaks 1–3 in the case of peptide (B). From this result, peak 2 and peak 3 were confirmed to be mono-sulfated compounds at the 62nd and at the 63rd Tyr, respectively.

The above results on the identification of sulfation sites are summarized below.

| Sulfated compound | Structure |
|---|---|
| Peak 1 (SEQ. ID. NO.: 12) | Val—Val—Tyr—Thr—Asp—Cys—Thr—Glu—Ser—Gly—Gln—Asn—Leu—Cys—Leu—Cys—Glu—Gly—Ser—Asn—Val—Cys—Gly—Gln—Gly—Asn—Lys—Cys—Ile—Leu—Gly—Ser—Asp—Gly—Glu—Lys—Asn—Gln—Cys—Val—Thr—Gly—Glu—Gly—Thr—Pro—Lys—Pro—Gln—Ser—His— |

-continued

| Sulfated compound | Structure |
|---|---|
| Peak 2 (SEQ. ID. NO.: 12) | Asn—Asp—Gly—Asp—Phe—Glu—Glu—Ile—Pro—Tyr—Tyr(SO$_3$H)—Tyr(SO$_3$H)—Leu—Gln<br>Val—Val—Tyr—Thr—Asp—Cys—Thr—Glu—Ser—Gly—Gln—Asn—Leu—Cys—Leu—Cys—Glu—Gly—Ser—Asn—Val—Cys—Gly—Gln—Gly—Asn—Lys—Cys—Ile—Leu—Gly—Ser—Asp—Gly—Glu—Lys—Asn—Gln—Cys—Val—Thr—Gly—Glu—Gly—Thr—Pro—Lys—Pro—Gln—Ser—His—Asn—Asp—Gly—Asp—Phe—Glu—Glu—Ile—Pro—Tyr—Tyr(SO$_3$H)—Tyr—Leu—Gln |
| Peak 3 (SEQ. ID. NO.: 12) | Val—Val—Tyr—Thr—Asp—Cys—Thr—Glu—Ser—Gly—Gln—Asn—Leu—Cys—Leu—Cys—Glu—Gly—Ser—Asn—Val—Cys—Gly—Gln—Gly—Asn—Lys—Cys—Ile—Leu—Gly—Ser—Asp—Gly—Glu—Lys—Asn—Gln—Cys—Val—Thr—Gly—Glu—Gly—Thr—Pro—Lys—Pro—Gln—Ser—His—Asn—Asp—Gly—Asp—Phe—Glu—Glu—Ile—Pro—Tyr—Tyr—Tyr(SO$_3$H)—Leu—Gln |

Example 11

Example of pharmacological tests (anti-thrombin activity: clotting assay)

Hirudin binds to blood coagulation factor thrombin in a 1:1 ratio to inhibit blood coagulation. Recently, the binding manner of hirudin and thrombin became clear by crystallography [T. J. Rydel et al., Science, 249, p277–280 (1990)]. The result shows that the C-terminal region of hirudin binds to thrombin in a wrapping manner, and this bond becomes stronger when the hydroxyl group of Tyr at 63rd position is sulfated, which is thought to be the cause of the increase in anti-thrombin activity.

Some of the compounds obtained by the present invention have stronger anti-thrombin activity compared with hirudins produced by conventional methods. Measurement of anti-thrombin activity was done by looking at anti-coagulant activity as an index using fibrinogen as the substrate. That is, the compounds were dissolved in 200 µl of 0.1 mM Tris-HCl buffer (pH 7.5) containing 0.1% polyethyleneglycol-6000, added 100 µl of human-thrombin prepared at 10 NIH units/ml in aforesaid buffer, were added, and the 200 µl of human-fibrinogen (product of Sigma) prepared at 6 mg/ml in aforesaid tris-hydrochloride buffer, and coagulation time of the reaction mixtures were measured. For measuring of coagulation times, coagulation time analyzer (Amelung KC10A) was used. Obtained values were converted into units by using a previously prepared thrombin standard curve. Graphs were prepared by plotting the converted values on the vertical axis, and the concentrations of the compounds on the horizontal axis. In graphs, the thrombin unit was defined as 100 at a compound concentration of 0. The concentration of compounds corresponding to 50 units were defined as 50% inhibitory concentration of compounds. Results are shown in Table 2.

TABLE 2

| Compounds | 50% Inhibition Concentration (ng/ml) | Potency |
|---|---|---|
| HV-1 (54–65) | 6608.3 | 1 |
| (A) | 14689.8 | 0.45 |
| (B) | 13829.7 | 0.48 |
| Sulfated form of (A) | 3396.6 | 1.95 |
| Sulfated form of (B) | | |
| peak 1 | 493.4 | 13.39 |
| peak 2 | 1018.5 | 6.49 |
| peak 3 | 4029.3 | 1.64 |
| (C) | 3753.5 | 1.76 |
| Sulfated form of (C) | 74.3 | 88.94 |

TABLE 2-continued

| Compounds | 50% Inhibition Concentration (ng/ml) | Potency |
|---|---|---|
| Sulfated form of (D) | 115.8 | 57.07 |
| Sulfated form of (E) | 148.8 | 44.41 |
| Sulfated form of (F) | 5015.1 | 1.32 |
| Sulfated form of (G) | 60.7 | 108.87 |
| Sulfated form of (H) | >200000 | <0.05 |
| (I) | 20019.4 | 0.83 |
| Sulfated form of (I) | 4078.1 | 1.62 |
| (J) | 98392.6 | 0.07 |
| (K) | 30187.4 | 0.21 |
| Sulfated form of (K) | 6451.0 | 1.02 |
| (L) | 15625.1 | 0.42 |
| Sulfated form of (L) | 3139.4 | 2.11 |
| (N) | 103092.4 | 0.06 |
| (O) | 35266.9 | 0.19 |
| (P) | 103888.1 | 0.06 |
| Sulfated form of (Q) | 3568.6 | 1.85 |
| (R) | 36094.5 | 0.18 |
| (S) | 99624.6 | 0.07 |
| Sulfated form of (T) | 793.9 | 8.32 |
| (U) | 47467.1 | 0.14 |
| (V) | 30420.1 | 0.22 |
| (W) | 34981.1 | 0.19 |
| Sulfated form of (X) | 3206.8 | 2.06 |
| (Y) | 153438.6 | 0.04 |
| hirudin HV-1 | 69.6 | 94.95 |
| hirudin HV-17 | 70.3 | 94.00 |
| Sulfated form of hirudin HV-17 | 64.0 | 103.26 |

[1]note: potency was calculated using definition that HV-1 (54–65) potency is 1.
HV-1 (54–65): H—Gly—Asp—Phe—Glu—Ile—Pro—Glu—Glu—Tyr—Leu—Gln—OH (SEQ. ID. NO.:13)
hirudin HV-1: Val—Val—Tyr—Thr—Asp—Cys—Thr—Glu—Ser—Gly—Gln—Asn—Leu—Cys—Leu—Cys—Glu—Gly—Ser—Asn—Val—Cys—Gly—Gln—Gly—Asn—Lys—Cys—Ile—Leu—Gly—Ser—Asp—Gly—Glu—Lys—Asn—Gln—Cys—Val—Thr—Gly—Glu—Gly—Thr—Pro—Lys—Pro—Gln—Ser—His—Asn—Asp—Gly—Asp—Phe—Glu—Glu—Ile—Pro—Glu—Glu—Tyr—Leu—Gln (SEQ. ID. NO.:14)

Example 12

Example of pharmacological tests (anti-thrombin activity, chromogenic assay)

Anti-thrombin activities were measured by measuring the degree of inhibition of thrombin's hydrolytic activity on synthetic substrate Chromozyme TH (Tocylglycil-prolylarginine-4-nitroanilideacetate). This reaction was carried out as follows. 350 pM human-thrombin (product of Sigma) was added to a buffer containing 0.1M Tris-HCl buffer (pH 8.5), 150 mM NaCl and 0.1% polyethyleneglycol-6000, followed by addition of hirudin HV-1, hirudin HV-17 and separated and collected sulfated hirudin HV-17 (peak 1, peak 2, peak 3), preincubation at 37° C. for 3 minutes. Here, the molar concentration of aforementioned human-thrombin was determined by the method of active site titration [G. W. Jameson et al., Biochem. J., 131, p107–117 (1973)] using 4-methylunberifenyl-p-guanidinobenzoate as substrate. After the pre-incubation, Chromozym TH (product of Boehringer-Mannheim) was added to a final concentration of 100 μM, and released p-nitroanilide was measured at the wave length of 405 nm, and the initial velocity of the hydrolytic reactions were measured for each of the abovementioned hirudins at various concentrations. From this initial velocity of hydrolytic reactions, the apparent dissociation constants Ki' were calculated by the method of S. R. Stone et al. [Biochemistry, 25, p4622–4628 (1986)]. The results are shown in Table 3.

These results show although hirudin HV-17 is less active than hirudin HV-1, sulfated hirudin HV-17 showed about twice as much activity a hirudin HV-1.

TABLE 3

| Polypeptide | Ki' (pM) | Potency |
|---|---|---|
| hirudin HV-1 | 6.4 | 1 |
| hirudin HV-17 | 16.8 | 0.38 |
| Sulfated form of hirudin HV-17 | | |
| peak 1 | 2.8 | 2.3 |
| peak 2 | 4.3 | 1.5 |
| peak 3 | 5.9 | 1.1 |

Example 13
Inhibitory action of sulfated peptides against thrombin induced death To male mice (20–25g), in non-anaesthesia, thrombin (15 NIH units/ 10 g) was administered intravenously, and the anti-thrombin activity of the tested compound was evaluated by observing the disappearance of roll over reflection and death as indexes. All the tested compounds were dissolved in saline and 0.05 ml/10 g were administered intravenously 5 min prior to the thrombin injection. The results are shown in Table 4.

TABLE 4

| Tested compound | Amount of administration (mg/kg weight) | Score* |
|---|---|---|
| Thrombin + Saline (15 NIH units/10 g weight) | | 1.7 |
| Thrombin + HV1 (15 NIH units/10 g weight) | 10 | 1.3 |
| | 20 | 0.6 |
| | 50 | 0.4 |
| Thrombin + sulfated (C) (15 NIH units/10 g weight) | 20 | 1.2 |
| | 50 | 0.8 |
| | 100 | 0.6 |

*Score
score 0: no disappearance of roll over reflection (apparently normal)
score 1: disappearance of roll over reflection, but no death within 20 minutes
score 2: death within 20 minutes Example 14
Prolongation of bleeding time Samples were injected into male mice (20–25g) via their tail vein under anaesthesia using pentobarbital (40 mg/kg i.p.). A puncture wound was made by inserting a 21 G needle (outer diameter 0.85 mm) into the other side of the tail vein 5 minutes after administration of test compounds and bleeding time of the wound was measured.

A filter was put on the wound with changes every 15 seconds. Bleeding time is defined as the time required until no red spot is observed on the filter paper. The result are shown in Table 5.

TABLE 5

| Tested compound | Amount of administration (mg/kg weight) | Bleeding time (sec) |
|---|---|---|
| Saline | | 148.5 ± 14.6 |
| HV-1 | 2 | 223.5 ± 15.6 |
| | 5 | 376.7 ± 20.2 |
| | 10 | 501.7 ± 47.1 |
| Sulfated (C) | 10 | 277.5 ± 31.5 |
| | 20 | 366.0 ± 23.0 |
| | 50 | 432.0 ± 33.3 |

In general, prolongation of bleeding time is one of the side effects of anti-coagulants. Here, the sulfated compound of the present invention was clear confirmed to have lower bleeding tendency than hirudin HV-1.

Example 15
Formulation (1) Capsules digestible in the intestine were prepared using sulfated (C) and (G) obtained in Example 4 with the following compositions, respectively.

| | (a) | (b) |
|---|---|---|
| Main ingredient (sulfated (C) or (G)) | 10 g | 5 g |
| Lactose | 2.5 g | 7.5 g |
| Hydroxypropylcellulose | 0.5 g | 0.5 g |

This oral drug may be administered to patients one to several times a day.

(2) 5 mg of lyophilized sulfated hirudin mutant HV-17 obtained in Example 10 was dissolved in 10 ml sterilized saline and filled in ampules to produce an intravenously injectable drug.

This drug may be administered to patients one to several times a day.

Industrial Applicability Among the peptides in the present invention, the sulfated compounds have extremely high anti-thrombin and anti-platelet activities, which are useful for therapy and prevention of acute deep venous thrombosis, pulmonary thromboembolism, acute arterial embolism of limbs, myocardial infarction etc. Thus, they are useful as anti-coagulants. Although non-sulfated compounds themselves have aforesaid anti-thrombin and anti-platelet activities, they are also useful for obtaining peptides of extremely high anti-thrombin and anti-platelet activities by sulfating hydroxyl group of tyrosine residues of said peptides.

Reference of microorganism deposit
1. E. coli RR1/pMTSHV17
    Organization of Deposition:
        Fermentation Research Institute,
        Agency of Industrial Science and Technology,
        Ministry of International Trade and Industry
    Address:
        1-1-3, Tsukuba-shi Higashi, Ibaraki-ken, Japan
    Date of Deposition:
        Feb. 6, 1991
    Deposition Number:
        FERM BP-3268

We claim:

1. A hirudin variant or a pharmaceutically acceptable salt thereof having the amino acid sequence of formula III:

D-R1-Phe-Glu-A-Ile-Pro-B-Tyr($R^a$)-Tyr($R^b$)-R2-C     (III)

wherein said hirudin variant has an amino acid sequence consisting of 12 amino acids or less;

A is Glu or Pro;

B is Glu, Tyr or Tyr ($SO_3H$);

Tyr($R^a$) and Tyr($R^b$) are independently selected from Tyr and Tyr ($SO_3H$);

Tyr ($SO_3H$) is a sulfated ester of tyrosine;

R1 is -Gly-Asp-, -Asp-, or a bond;

with the proviso that at least one of B, Tyr($R^a$) and Tyr($R^b$) is Tyr ($SO_3H$);

D is bonded to the N-terminal amino group of R1 and is selected from the group consisting of a hydrogen atom, an alkanoyl group, an alkanoyl group bearing an OH group, a carboxyalkanoyl group, a carboxyalkanoyl group bearing an OH group, an alkoxycarbonyl alkanoyl group, an alkenoyl group, a carboxyalkenoyl group, an alkoxycarbonyl alkenoyl group, and a carbamoylalkenoyl group;

R2 is optionally present and is Leu or Asp; and

C optionally replaces the C-terminal hydroxyl of the peptide and is selected from the group consisting of an —$NH_2$ group, a ($C_1$–$C_5$-alkyl)amino group, an amino acid, a $C_1-C_5$ alkyl ester of an amino acid, an amino acid amide group, a $(C_1-C_5$-alkyl)amide of an amino acid, an amino sulfonic acid group, an aminosulfonamide group, an amino alcohol group, an amino phosphoric acid group, an amino phosphoric acid ester, and an aminophosphonamide group.

2. The hirudin variant or pharmaceutically acceptable salt of claim 1, wherein C is present and is selected from the group consisting of —$NH_2$, —$NHCH_3$, —$NHC_2H_5$, a naturally occurring amino acid, D-Glu, α-amino adipic acid, Asu, Glu—$OC_2H_5$, Glu($OC_2H_5$)—$OC_2H_5$, Asu (OMe)-OMe, Glu—$NH_2$, Gln—$NH_2$, Asu ($NH_2$)—$NH_2$, Glu—$NHC_2H_5$, Gln—$NHC_2H_5$, —NH—$CH_2$—$SO_3H$, Tau, —NH—$(CH_2)_3$—$SO_3H$, —NH—$CH_2$—$SO_2NH_2$, Tau—$NH_2$, —NH—$(CH_2)_2$—OH, —NH—$(CH_2)_3$—OH, Leu-ol, —NHPO$(OH)_2$, —NHPO$(OC_2H_5)_2$, —NHPO$(OPh)_2$, and —NHPO $(NH_2)_2$.

3. The hirudin variant or a pharmaceutically acceptable salt of claim 1, wherein D is selected from the group consisting of $CH_3CO$—, $CH_3CH_2CH_2CO$—, $(CH_3)_2CH_2CO$—, $CH_3CH(OH)CO$—, $HOOCCH_2CH_2CO$—, $HOOC(CH_2)_3CO$—, $HOOCCH(OH)CH_2CO$—, $EtOOCCH_2CH_2CO$—, $H_2NOCCH_2CH_2CO$—, $CH_2$=CHCO—, $CH_3(CH_2)_7CH$=$CH(CH_2)_7CO$—, maleinyl, HOOCCH=CHCO—, EtOOCCH=CHCO—, and $H_2NOCCH$=CHCO— alkanoyl.

4. The hirudin variant or pharmaceutically acceptable salt of claim 3, wherein D is selected from the group consisting of acetyl ($CH_3CO$—), butyryl ($CH_3CH_2CH_2CO$—), isobutyryl (($CH_3)_2CH_2CO$—), lactinyl ($CH_3CH(OH)CO$—), succinyl ($HOOCCH_2CH_2CO$—) glutaryl ($HOOC(CH_2)_3CO$—), malicyl ($HOOCCH(OH)CH_2CO$—), ethoxy carbonyl propionyl ($EtOOCCH_2CH_2CO$—) carbamoyl propionyl ($H_2NOCCH_2CH_2CO$—), acryl ($CH_2$=CHCO—), oleinyl ($CH_3$ $(CH_2)_7CH$=$CH(CH_2)_7CO$—), maleinyl, furmalyl (HOOCCH=CHCO—), ethoxy carbonyl acrylyl (EtOOCCH=CHCO—), and carbamoylacrylyl ($H_2NOCCH$=CHCO—) alkanoyl.

5. The hirudin variant according to any of claims 1 and 2–4, wherein B is Glu or Tyr, and wherein each of Tyr($R^a$) and Tyr($R^b$) is Tyr($SO_3H$).

6. A method for preparing said hirudin variant of any one of claims 1 and 2–4 wherein at least one of Tyr($R^a$) and Tyr($R^b$) is Tyr ($SO_3H$), which comprises preparing a hirudin peptide according to any of claims 1 and 2–4 having the same amino acid sequence as said hirudin peptide, wherein each of Tyr($R^a$) and Tyr($R^b$) is tyrosine, and then sulfating at least one of Tyr($R^a$) and Tyr($R^b$) therein in a solution of a sulfur trioxide complex selected from the group consisting of pyridine-sulfur trioxide complex, dioxane-sulfur trioxide complex, thioxane-sulfur trioxide complex, bis(2-chloroethyl) ether-sulfur trioxide complex, 2-methylpiperidine-sulfur trioxide complex, quinoline-sulfur trioxide complex and a mixture of at least two of said complexes.

7. The method according to claim 6, wherein B is Glu or Tyr($SO_3H$) and both of said Tyr(R) residues are Tyr($SO_3H$), and wherein said sulfating is carried out by employing a sulfur trioxide complex selected from the group consisting of pyridine sulfur trioxide complex, dioxane sulfur trioxide complex, thioxane sulfur trioxide complex, and bis(2-chloroethyl)ether sulfur trioxide complex.

8. A method for preparing said hirudin variant of any one of claims 1 and 2–4, wherein B is Glu or Tyr($SO_3H$) and each of Tyr($R^a$) and Tyr($R^b$) is Tyr($SO_3H$), which comprises preparing a hirudin peptide of one of claims 1 and 2–4 having the same amino acid sequence as said hirudin peptide, wherein each of Tyr($R^a$) and Tyr($R^b$) is tyrosine, and then sulfating the Tyr($R^a$) and Tyr($R^b$) residues therein in a pyridine solution which contains sulfur trioxide and which also contains at least one compound selected from the group consisting of quinoline, 2-methylpyridine, dioxane, thioxane and bis(2-chloroethylether).

* * * * *

UNITED STATES PATENT AND TRADEMARK OFFICE
CERTIFICATE OF CORRECTION

PATENT NO. : 5,767,235
DATED : June 16, 1998
INVENTOR(S) : Nukui et al.

It is certified that error appears in the above-identified patent and that said Letters Patent is hereby corrected as shown below:

On the Cover Page:

Item [19] change "Nukui et al." to --Muramatsu et al.--

[75] Inventors
Please list the inventor's names in accordance with the request for the International Application (Form PCT/RO/101)

--Ryo Muramatsu; Akiko Sukesada; Satoru Misawa all of Toda; Eriko Nukui; Koichi Wada; Masaharu Nakano; Tadanori Morikawa, all of Takaoka; Kyoichi Kobashi, Toyama, all of Japan--

UNITED STATES PATENT AND TRADEMARK OFFICE
CERTIFICATE OF CORRECTION

PATENT NO. : 5,767,235
DATED : June 16, 1998
INVENTOR(S) : Nukui et al.

It is certified that error appears in the above-identified patent and that said Letters Patent is hereby corrected as shown below:

[73] Assignees
    change "Nippon Mining Company Limited" to --Japan Energy Corporation--

Signed and Sealed this

Fourteenth Day of September, 1999

Attest:

Q. TODD DICKINSON

*Attesting Officer*   Acting Commissioner of Patents and Trademarks